US007882167B2

(12) United States Patent
Goldberger et al.

(10) Patent No.: US 7,882,167 B2
(45) Date of Patent: Feb. 1, 2011

(54) COMPLEXITY-BASED DYNAMICAL ANALYSIS OF A NETWORK

(75) Inventors: Ary L. Goldberger, Newton Centre, MA (US); Chung-Kang Peng, Sharon, MA (US); Madalena D. Costa, Boston, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 1202 days.

(21) Appl. No.: 11/483,172

(22) Filed: Jul. 10, 2006

(65) Prior Publication Data

US 2007/0066906 A1 Mar. 22, 2007

Related U.S. Application Data

(63) Continuation-in-part of application No. 11/356,044, filed on Feb. 17, 2006, now Pat. No. 7,601,124.

(60) Provisional application No. 60/654,079, filed on Feb. 18, 2005.

(51) Int. Cl.
 *G06F 15/16* (2006.01)
(52) U.S. Cl. ....................................................... 709/200
(58) Field of Classification Search .................. 709/223, 709/200, 205, 224, 218
See application file for complete search history.

(56) References Cited

U.S. PATENT DOCUMENTS

| | | | |
|---|---|---|---|
| 5,277,189 A | | 1/1994 | Jacobs |
| 5,892,937 A | * | 4/1999 | Caccavale .................. 711/135 |
| 6,490,478 B1 | | 12/2002 | Zhang et al. |
| 6,631,291 B2 | | 10/2003 | Viertio-Oja et al. |
| 2003/0163057 A1 | | 8/2003 | Flick et al. |
| 2005/0049911 A1 | * | 3/2005 | Engelking et al. ............. 705/11 |
| 2007/0016418 A1 | * | 1/2007 | Mehrotra et al. ............ 704/240 |

OTHER PUBLICATIONS

Costa, et al., "Broken Asymmetry of the Human Heartbeat: Loss of Time Irreversibility in Aging and Disease," PRL 95, 198102 (Nov. 2004).

(Continued)

*Primary Examiner*—Firmin Backer
*Assistant Examiner*—Ebrahim Golabbakhsh
(74) *Attorney, Agent, or Firm*—Sterne, Kessler, Goldstein & Fox P.L.L.C.

(57) ABSTRACT

In a subject undergoing therapeutic intervention, efficacy of the therapeutic intervention is assessed based on a series of physiologic data associated with the subject. The series of physiologic data is analyzed to produce a measure of complexity. The complexity measure is then compared to a control. The efficacy of the therapeutic intervention is assessed based on the comparison of the complexity measure to the control. The control may be, for example, a complexity measure taken prior to initiation of the therapeutic intervention, a complexity measure taken from a different subject, or a predetermined threshold value. The measure of complexity is generated using, for example, a multiscale entropy measurement (MSE), a time asymmetry measurement, and/or an information-based similarity measurement. An increase in complexity indicates a positive effect of the therapeutic intervention, while a decrease in complexity indicates a negative effect of the therapeutic intervention. Stability of a non-biologic network, such as a computer network, communications network or transportation network can also be assessed.

14 Claims, 32 Drawing Sheets

OTHER PUBLICATIONS

Costa, et al., "Multiscale Entropy Analysis of Complex Physiologic Time Series," PRL, vol. 89, No. 6, 068102 (Aug. 2002).

Costa, et al., "Multiscale Entropy Analysis of Complex Heart Rate Dynamics: Discrimination of Age and Heart Failure Effects," Computers in Cardiology 30:705-708 (2003).

Costa, et al., "Noise and Poise: Enhancement of postural complexity in the elderly with a stochastic-resonance-based therapy," EPL, 77, 68008 (Mar. 2007).

Yang, et al., "Information categorization approach to literary authorship disputes," Physica A 329, 473-483 (Apr. 2003).

Costa, et al., "Multiscale entropy analysis of human gait dynamics," Physica A 330, 53-60 (2003).

Yang, et al., "Linguistic Analysis of the Human Heartbeat Using Frequency and Rank Order Statistics," PRL vol. 90, No. 10, 108103 (Mar. 2003).

"Costa, Goldberger, and Peng Reply:" PRL vol. 91, No. 11 (Sep. 2003).

"Costa, Goldberger, and Peng Reply:" PRL vol. 92, No. 8 (Feb. 2004).

"Yang et al. Reply:" PRL vol. 92, No. 10 (Mar. 2004).

Costa, et al., "Multiscale entropy analysis of biological signals," PRL 71, 021906 (2005).

Suder, et al., "One-dimensional, nonlinear determinism characterizes heart rate pattern during paced respiration," Am. J. Physiol. Hear Circ. Physiol. 275:1092-1102 (1998).

Hoekstra, et al., "Non-linear time series analysis: methods and applications to atrial fibrillation," Ann. Ist. Super. Sanita, vol. 37, n. 3, pp. 325-333 (2001).

Yang, et al., "Information-Based Similarity Index," [online, Oct. 27, 2004] retrieved from the internet: URL: http://physionet.org/physiotools/ibs/doc/.

International Search Report for PCT/US06/05581, mailed Sep. 5, 2007.

Written Opinion of the International Searching Authority for PCT/US06/05581, mailed Sep. 5, 2007.

Goldberger et al., "What is physiologic complexity and how does it change with aging and disease?" Neurobiology of Aging 23, 23-26 (2002).

Bergman, U.M., "Stationarity and nonstationarity in single-equation regression analysis," Department of Economics, Lund University (2003).

Costa, et al., "Multiscale Entropy to Distinguish Physiologic and Synthetic RR Time Series," Computers and Cardiology 29:137-140 (2002).

Costa et al., "Multiscale Entropy Analysis (MSE)," [online, retrieved on Feb. 2, 2005], retrieved from the internet: URL: http://www.physionet.org/physiotools/mse/.

"Rational drug design," [online, retrieved on Dec. 23, 2004], retrieved from internet: URL: http://www.wellcome.ac.uk/en/genome/tacklingdisease/hg09b002.html.

Marton MJ, et al. "Drug target validation and identification of secondary drug target effects using DNA microarrays," Nat Med. 1998, Nov. 4(11):1235-6.

Henry, C.M., "Structure-based Drug Design," Science & Technology Pharmaceuticals, vol. 79, No. 23, pp. 69-74, Jun. 4, 2001.

* cited by examiner

COMPLEXITY-BASED DYNAMICAL ANALYSIS OF A NETWORK

RELATED APPLICATIONS

This application is a continuation-in-part of U.S. application Ser. No. 11/356,044, filed Feb. 17, 2006, which claims priority to U.S. Provisional Appl. No. 60/654,079, filed Feb. 18, 2005, both of which are incorporated herein by reference.

STATEMENT REGARDING FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention relates generally to analyzing time series data, and more specifically, to non-invasively assessing therapeutic toxicity and efficacy from physiologic measurements.

2. Related Art

The physiologic systems of a living organism generate complex fluctuations in their output signals. The complex fluctuations (also referred to as "complexity") arise from the interaction of a myriad of structural units and regulatory feedback loops that operate over a wide range of temporal and spatial scales. This interaction reflects the organism's ability to adapt to the stress of everyday life.

Being able to quantify or model physiologic complexity would provide insight into the underlying dynamics of an organism. For example, a decrease in physiologic complexity can be symptomatic of a pathologic process. However, contemporary mathematical approaches to measuring the complexity of biological signals fail to account for the multiple time scales inherent in such time series. These approaches have yielded contradictory findings when applied to real-world datasets obtained in health and disease states.

Conventional biomedical approaches to designing therapeutic interventions for pathologic processes are also plagued with several shortcomings. Current screening tests and assays for the efficacy and toxicity of pharmacologic and non-pharmacologic interventions are based primarily on local effects and on the measurement of a limited range of markers. Such measures fail to account for systemic effects associated with integrative feedback (also referred to as a "systems biology approach"). Thus, a drug might appear to have beneficial effects in the short-term, or based on site-specific actions. However, more sustained use might be associated with lethal toxicities not detected in the conventional evaluation. The literature is replete with examples of such unexpected toxicities, including the notorious examples of cardiac "antiarrhythmic" drugs that have "proarrhythmic" effects and increase the risk of sudden cardiac arrest.

A fundamental problem in the development of novel therapeutic agents and the ongoing monitoring of approved drugs, as well as non-pharmacologic interventions, is the sensitive assessment of their systemic safety and efficacy. Current methodologies for evaluating both efficacy and toxicity, however, largely fail to account for the effects on integrative physiologic function.

Therefore, a need exists to develop a technology that can overcome the aforementioned limitations and provide a more efficient and cost-effective technique and/or methodology for evaluating complexity and/or therapeutic interventions.

SUMMARY OF THE INVENTION

The present invention includes a method, system and computer program product for assessing system complexity via a panel of measurements. According to embodiments of the present invention, these measurements are used to detect aging, pathology, toxicity, and/or efficacy of therapeutic intervention, or the like.

In an embodiment, a panel of dynamical measurements quantifies different aspects of physiologic complexity and information content. The panel includes, but is not limited to, multiscale entropy (MSE), time asymmetry, and information-based similarity metrics.

In an embodiment, a series of physiologic data is accessed from non-invasive and/or invasive measurements that are taken from a subject. One or more of the measurements from the panel are used to quantify the system's complexity and its information content by examination of the physiologic time series. The computed complexity-based measurement(s) are compared to a threshold parameter(s) and/or a template curve of complexity values over multiple scales. If the threshold parameter(s) and/or the values of the template curve exceed the computed measurements, a loss of complexity is detected. Otherwise, no loss of complexity is detected, or a gain in complexity is detected if the computed complexity measurement(s) exceed the threshold parameter(s).

In an embodiment, a loss of complexity is associated with aging or a pathological condition. A gain in complexity is associated with an improvement from a pathological condition.

In an embodiment, one or more measurements from the panel can be applied to quantify the effects of drug and non-pharmacologic intervention. As such, interventions that enhance system complexity are associated with therapeutic effects, and interventions that degrade system complexity are associated with adverse effects.

One type of measurement for quantifying physiologic complexity and information content is the MSE approach. MSE approach can be applied to investigate the degree of complexity in physiologic signals and other time series that have correlations at multiple spatial and temporal scales. The results of the MSE approach can be applied to differentiate time series which are the output of different dynamical systems or are representative of different states of the same system. In particular, the MSE method can be applied to discriminate time series obtained from healthy and unhealthy subjects, younger and elderly subjects, 1-over-frequency (1/f) noise and white noise time series, etc.

In an embodiment, physiologic time series data is gathered from a subject. The time series data is processed to compute multiple coarse-grained time series. An entropy measure (e.g., sample entropy) is calculated for each coarse-grained time series plotted as a function of the scale factor. The plotted function is herein referred to as an MSE curve. In order to determine whether the complexity of the system has increased, decreased, or remained constant, the plotted MSE curve is compared to a template curve, which, according to the aims of the specific study, can be: (i) the curve obtained from the MSE analysis of a representative group of healthy subjects connecting the mean entropy values for each scale; or (ii) the MSE curve for a time series obtained from the subject being studied in an earlier state of the disease or prior to the initiation of drug or other non-pharmacologic therapy. The two MSE curves are compared according to the following rules: (i) if for the majority of scales, the values of entropy are higher for time series a than b, then time series a is more complex than time series b; and (ii) a monotonic decrease of the values of entropy indicates that the structure of the time series is similar to that of uncorrelated random noise time series which are the least complex of all.

In an embodiment, the MSE approach is applied to the cardiac interbeat interval time series of healthy subjects, those with congestive heart failure (CHF), and those with atrial fibrillation (AF). The MSE approach shows that healthy dynamics are the most complex. Under pathologic conditions, the structure of the time series' variability may change in two different ways. One dynamical route to disease is associated with loss of variability and the emergence of more regular patterns (e.g., heart failure). The other dynamical route is associated with more random types of outputs (e.g., atrial fibrillation). In both cases, a decrease in system complexity occurs under pathologic conditions.

When applied to simulated time series, the MSE approach reveals that correlated random signals (e.g., 1/f noise time series) are more complex than uncorrelated random signals (e.g., white noise time series). These results are consistent with the presence of long-range correlations in 1/f noise time series but not in white noise time series.

In an embodiment, the MSE approach is applied to compare the complexity of an executable computer program versus a compressed non-executable computer data file, and the complexity of selected coding versus non-coding DNA sequences. The MSE approach reveals that the executable computer program has higher complexity than the non-executable computer data file. Similarly, the MSE approach reveals that the non-coding sequences are more complex than the coding sequences examined. As such, the present invention supports recent in vitro and in vivo studies suggesting, contrary to the "junk DNA" theory, that non-coding sequences contain important biological information.

A second type of measurement useful to compare different time series is the time asymmetry approach. The time asymmetry approach can be applied to physiologic signals and other time series to produce a measure that quantifies the degree of temporal irreversibility of a signal over multiple spatial and/or temporal scales. In an embodiment, a physiologic time series $X=\{x_1, x_2, \ldots, x_N\}$ gathered from a subject is processed to compute multiple coarse-grained time series according to the equation $y_\tau(i)=(x_{\tau+i}-x_i)/\tau$ with $i \leq N-\tau$. Next, the histogram for each coarse-grained time series is calculated. For the study of heart rate time series, the inverse of the electrocardiographic Holter recording sample frequency is used as the histogram's bin size, denoted as $\Delta$. Of note, the histogram is a function $H(n)$ that associates the number of data points between $n\Delta$ and $(n+1)\Delta$ to each $n \epsilon N$. In an embodiment, a measure of the degree of irreversibility of each coarse-grained time series is calculated according to the equation:

$$\hat{A}(\tau) = \frac{\sum_{n>0} H(n) \times \ln[H(n)] - H(-n) \times \ln[H(-n)]}{\sum_{n \neq 0} H(n) \times \ln[H(n)]}$$

The multiscale asymmetry index ($A_I$) is computed from the following equation:

$$A_I = \sum_{\tau=1}^{L} \hat{A}(\tau).$$

In embodiments, the computed $A_I$ is compared to a threshold $A_T$ to determine an increase, decrease, or consistency in physiologic complexity.

A third type of measurement for quantifying physiologic complexity and information content is the information-based complexity approach. The information-based similarity approach is based on rank order statistics of symbolic sequences to investigate the profile of different types of physiologic dynamics. This approach can be applied to physiologic signals and other series to produce a measure that incorporates information from multiple spatial and temporal scales. In an embodiment, a time series of physiologic data gathered from a subject is compared to a time series of a prototypically healthy subject. Each physiologic time series is mapped to a binary time series. In the case of the cardiac interbeat interval time series, each pair of consecutive interbeat intervals is mapped to the symbols 0 or 1 depending on whether the difference between the two intervals is $\leq 0$ or $<0$. In an embodiment, an m-bit word is defined as sequences of m consecutive symbols. Each m-bit word represents a unique pattern of fluctuations in the time series. By shifting one data point at a time, a collection of m-bit words are produced over the whole time series. Next, the occurrences of different words are counted and, the different words are sorted according to descending frequency. After a rank-frequency distribution has been produced for both time series, a measurement of similarity between the two signals is defined by plotting the rank number of each m-bit word in the first time series against that of the second time series. The average deviation of these scattered points away from a diagonal line is a measure of the "distance" between these two time series. Greater distance indicates less similarity and less complexity, and less distance indicates greater similarity and greater complexity.

Thus, in an embodiment, the similarity measurement is applied to quantify physiologic complexity. For example, two time series obtained before and after an intervention are compared to a time series of a prototypically healthy subject. If the distance between the time series of a prototypically healthy subject and the time series of a subject obtained before a pharmacologic or non-pharmacologic intervention is larger than the distance between the time series of a prototypically healthy subject and the time series obtained after the intervention, then the effect of the intervention is a decrease in the system's complexity. If the distance between the time series of a prototypically healthy subject and the time series of a subject obtained before a pharmacologic or non-pharmacologic intervention is smaller than the distance between the time series of a prototypically healthy subject and the time series obtained after the intervention, then the effect of the intervention is an increase in the system's complexity. Finally, if there is no difference between the distances calculated before and after the intervention, then the intervention does not change the complexity of the system.

In another embodiment, the invention is used to assess the stability of the output of non-biologic networks. For example, the invention can be used to assess the stability of the output of the global Internet, a wide area network (WAN), a local area network (LAN), a Web server, other telecommunications networks, electricity flow in a power grid, as well as systems for managing air traffic flow, automotive traffic flow, shipping traffic in busy sea ports, rail traffic flow, and the like. In such environments, a loss of complexity in the output of the system may be a marker of a breakdown of network stability and possibly on an impending catastrophic failure.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable one skilled in the pertinent art(s) to make and use the invention. In the drawings, generally, like reference numbers indicate identical or functionally or structurally similar elements. Additionally, generally, the leftmost digit(s) of a reference number identifies the drawing in which the reference number first appears.

Figures 8A, 8B:
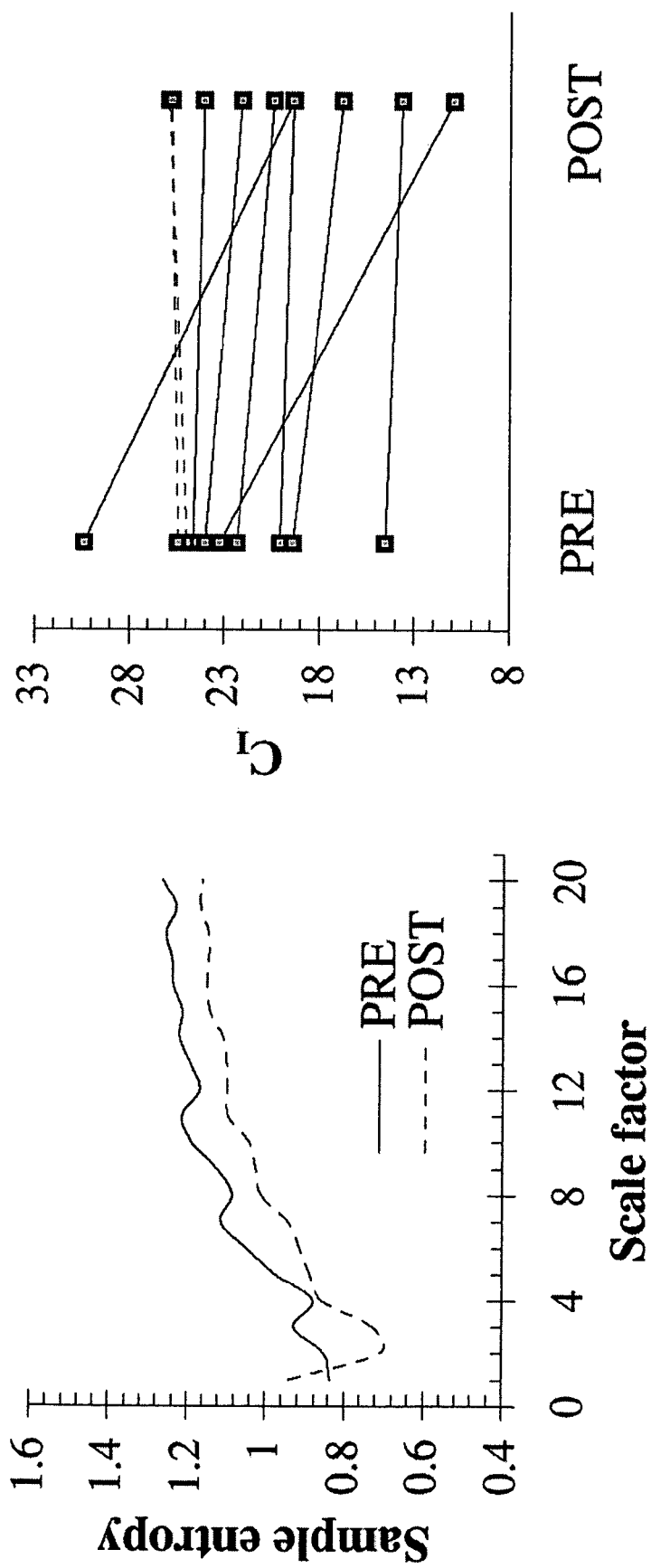

FIGS. 8A and 8B illustrate MSE results for the interbeat interval time series obtained before (PRE) and after (POST) treatment onset with the cardiac antiarrhythmic drug encainide. FIG. 8A presents MSE curves for the time series obtained from one representative subject. FIG. 8B presents complexity indexes $C_I$ for a randomly selected subset of the NIH Cardiac Arrhythmia Suppression Trial RR Interval Sub-Study Database comprising ten subjects treated with encainide. The NIH Cardiac Arrhythmia Suppression Trial RR Interval Sub-Study Database is available at http://www.physionet.org/physiobank/database/crisdb/. Solid lines were used when complexity decreased after treatment onset. Dotted lines were used when complexity increased after treatment onset.

Figures 9A, 9B:
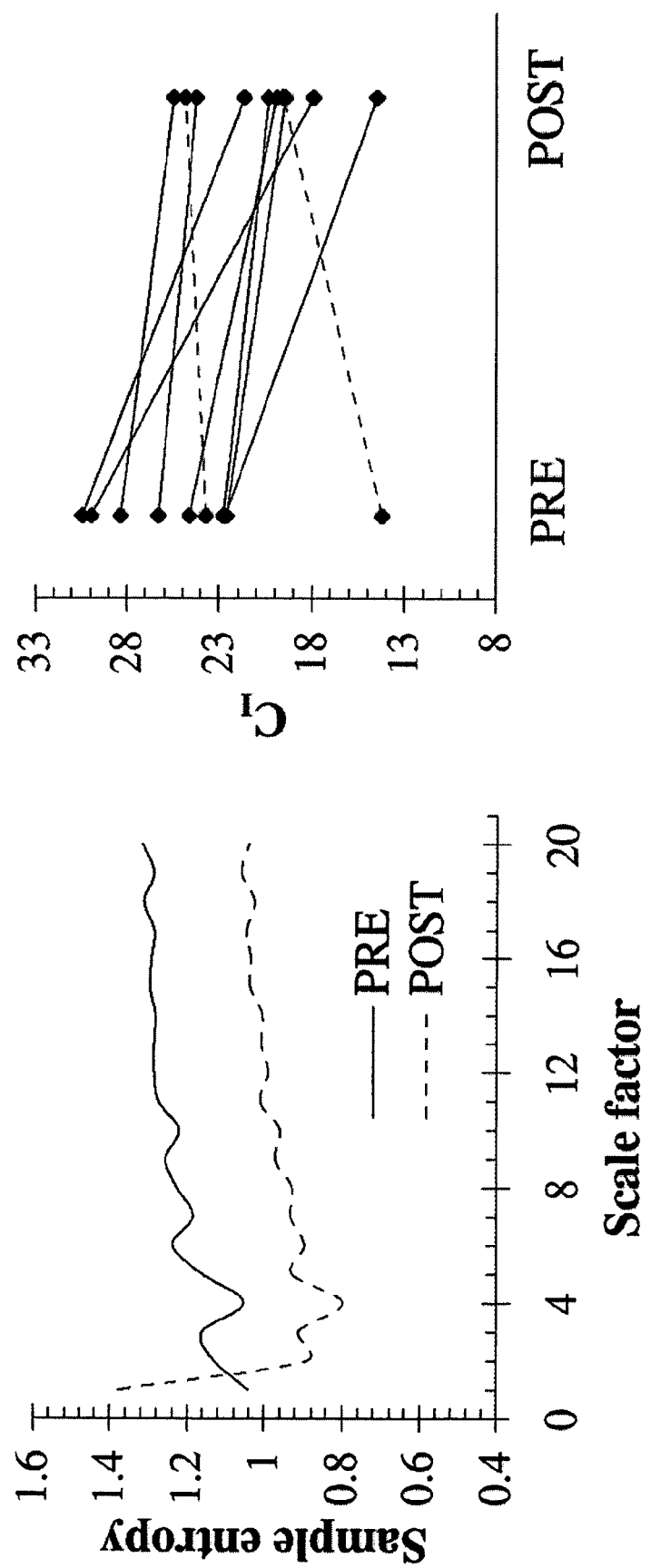

FIGS. 9A and 9B illustrate MSE results for the interbeat interval time series obtained before (PRE) and after (POST) treatment onset with the cardiac antiarrhythmic drug flecainide. FIG. 9A presents the MSE curves for the time series obtained from one representative subject. FIG. 9B presents complexity indexes $C_I$ for a randomly selected subset of the NIH Cardiac Arrhythmia Suppression Trial RR Interval Sub-Study Database comprising ten subjects treated with flecainide. Solid lines were used when complexity decreased after treatment onset. Dotted lines were used when complexity increased after treatment onset.

Figure 10B:
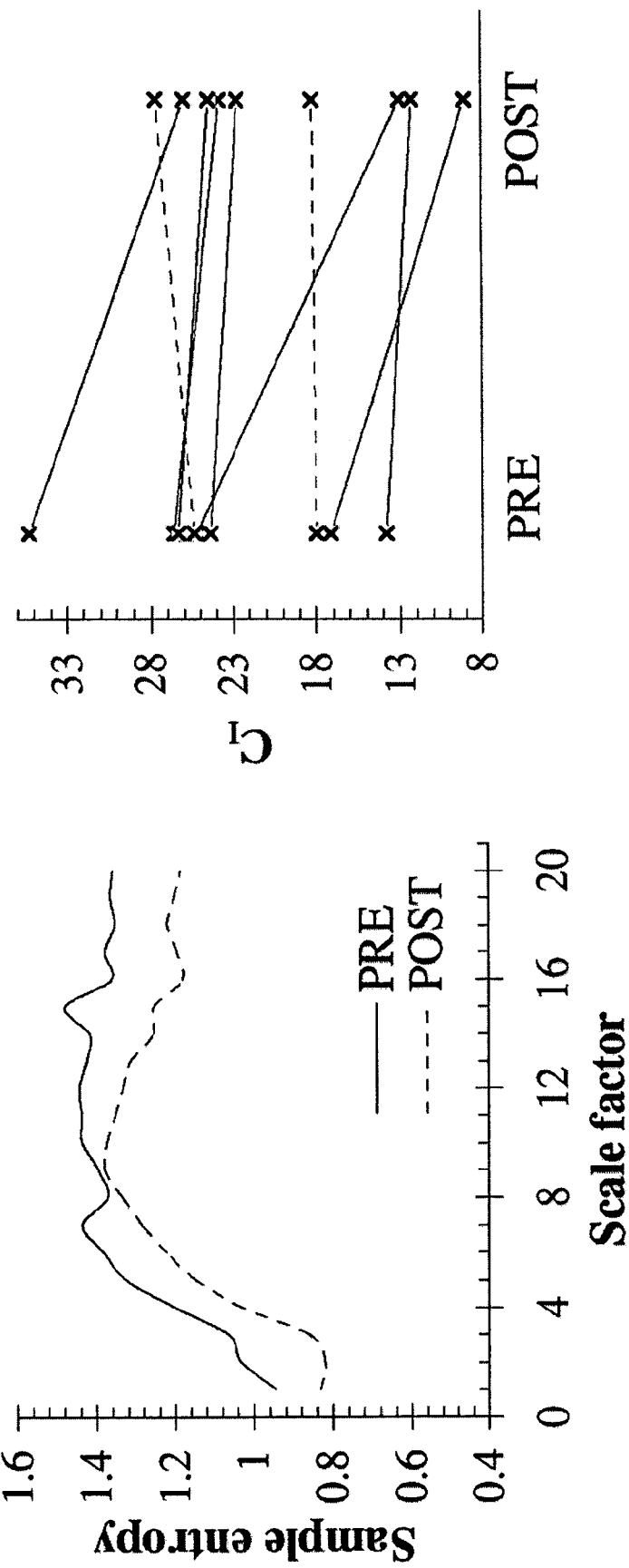
Figure 10A:
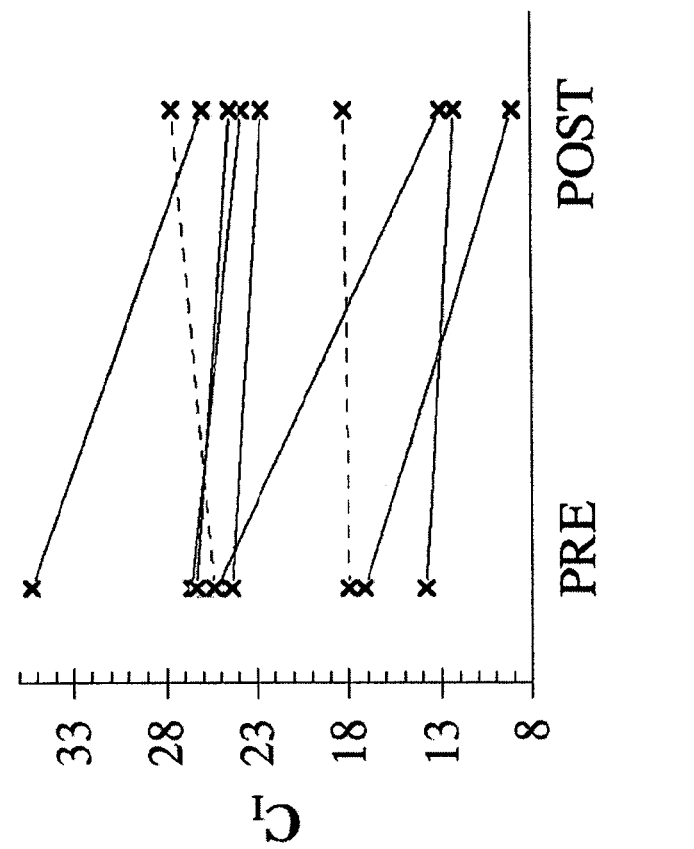

FIGS. 10A and 10B illustrate MSE results for the interbeat interval time series obtained before (PRE) and after (POST) treatment onset with the cardiac antiarrhythmic drug moricizine. FIG. 10A presents MSE curves for the time series obtained from one representative subject. FIG. 10B presents complexity indexes $C_I$ for a randomly selected subset of the NIH Cardiac Arrhythmia Suppression Trial RR Interval Sub-Study Database comprising ten subjects treated with moricizine. Solid lines were used when complexity decreased after treatment onset. Dotted lines were used when complexity increased after treatment onset.

Figure 11A:
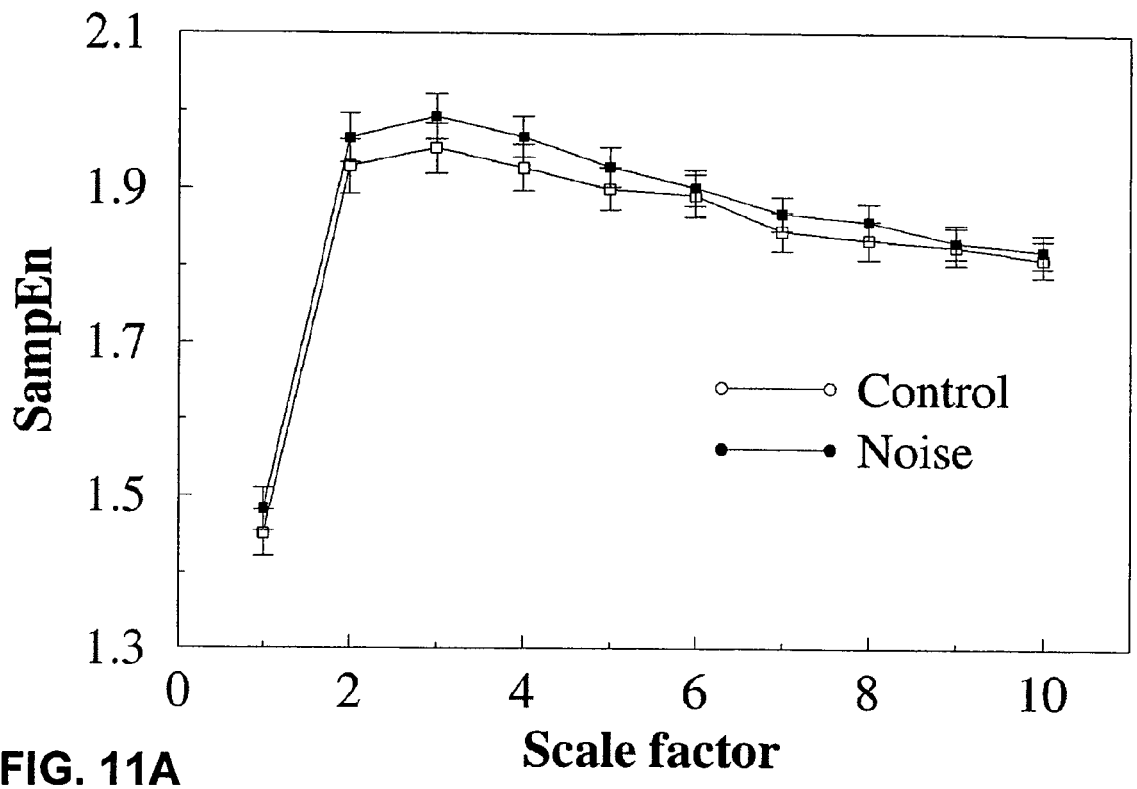
Figure 11B:
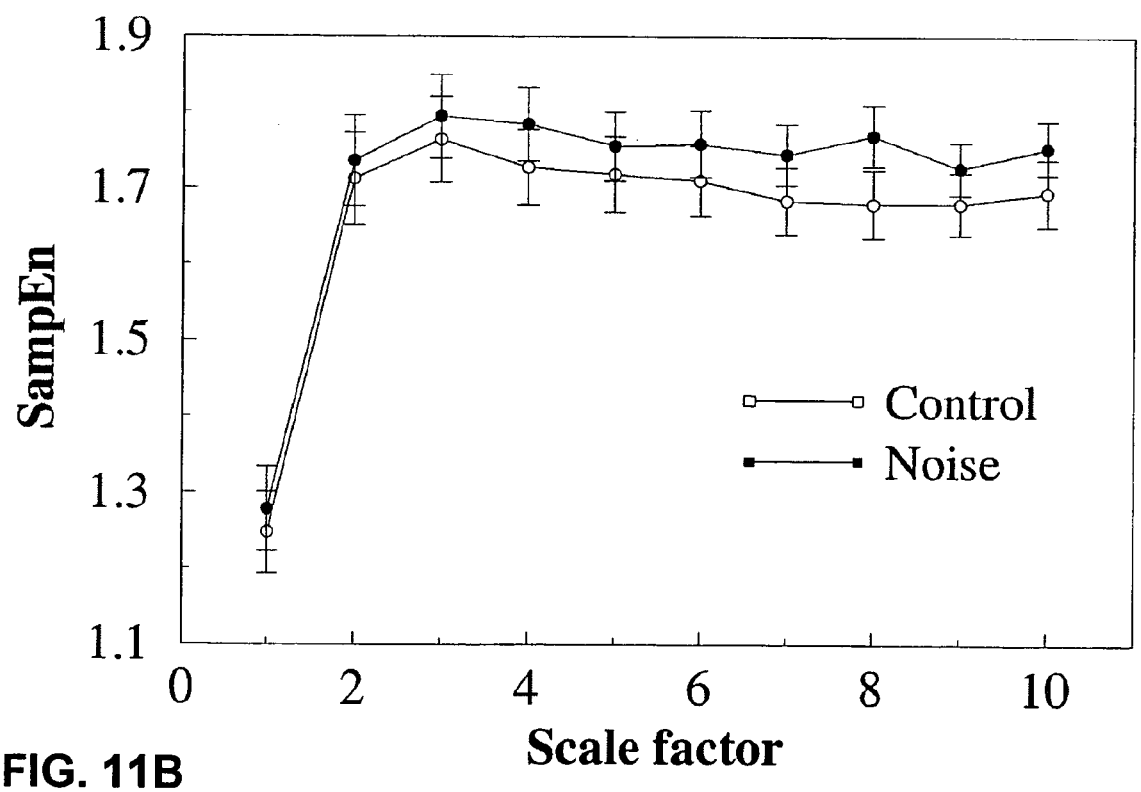

FIGS. 11A and 11B show MSE results for the center of pressure sway time series of young (FIG. 11A) and elderly (FIG. 11B) subjects before and during the application of subsensory noise to the sole of the feet.

Figure 12:
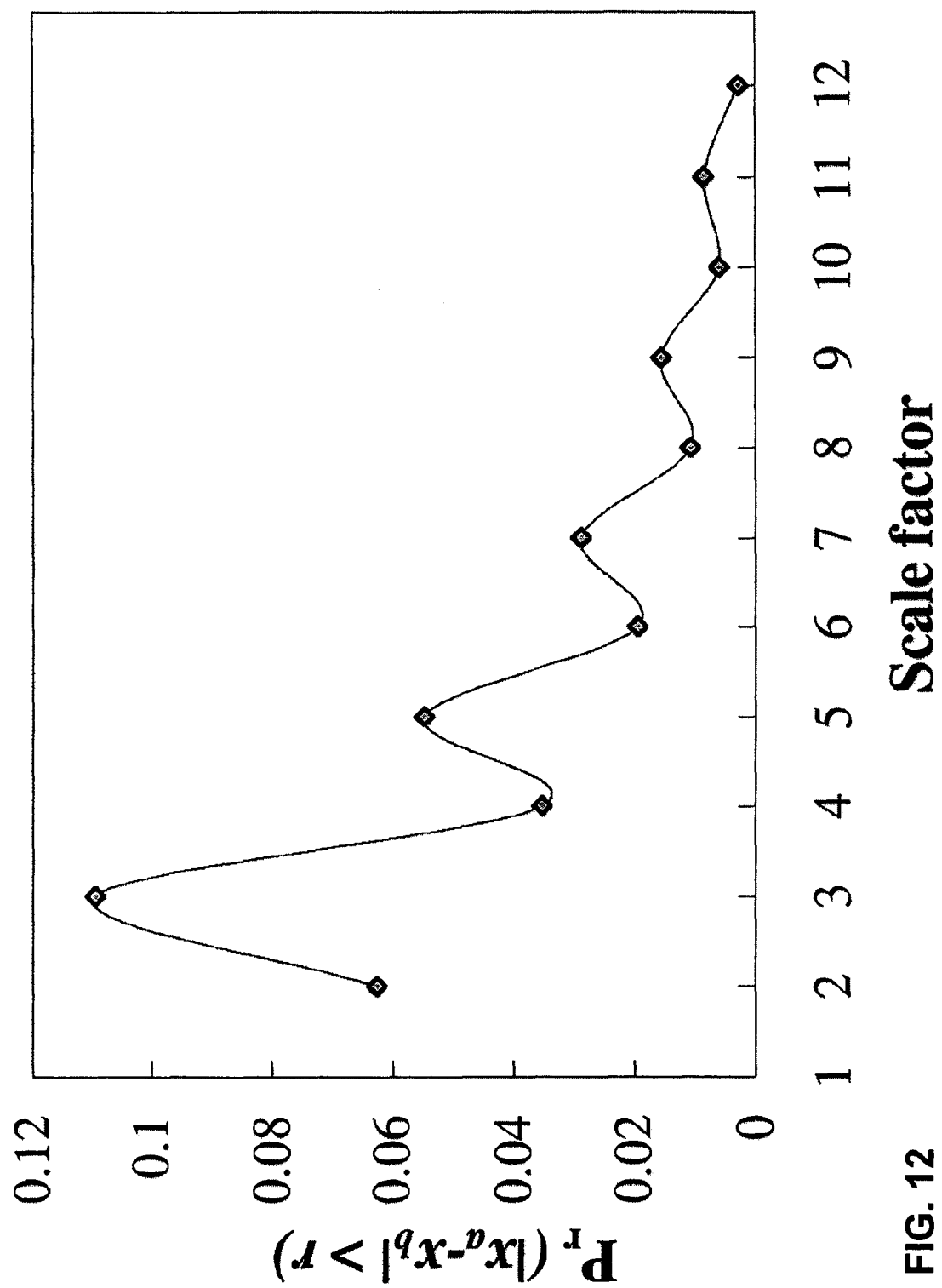

FIG. 12 illustrates the probability of distinguishing two randomly chosen data points from a coarse-grained time series of a binary discrete time series.

Figure 13:
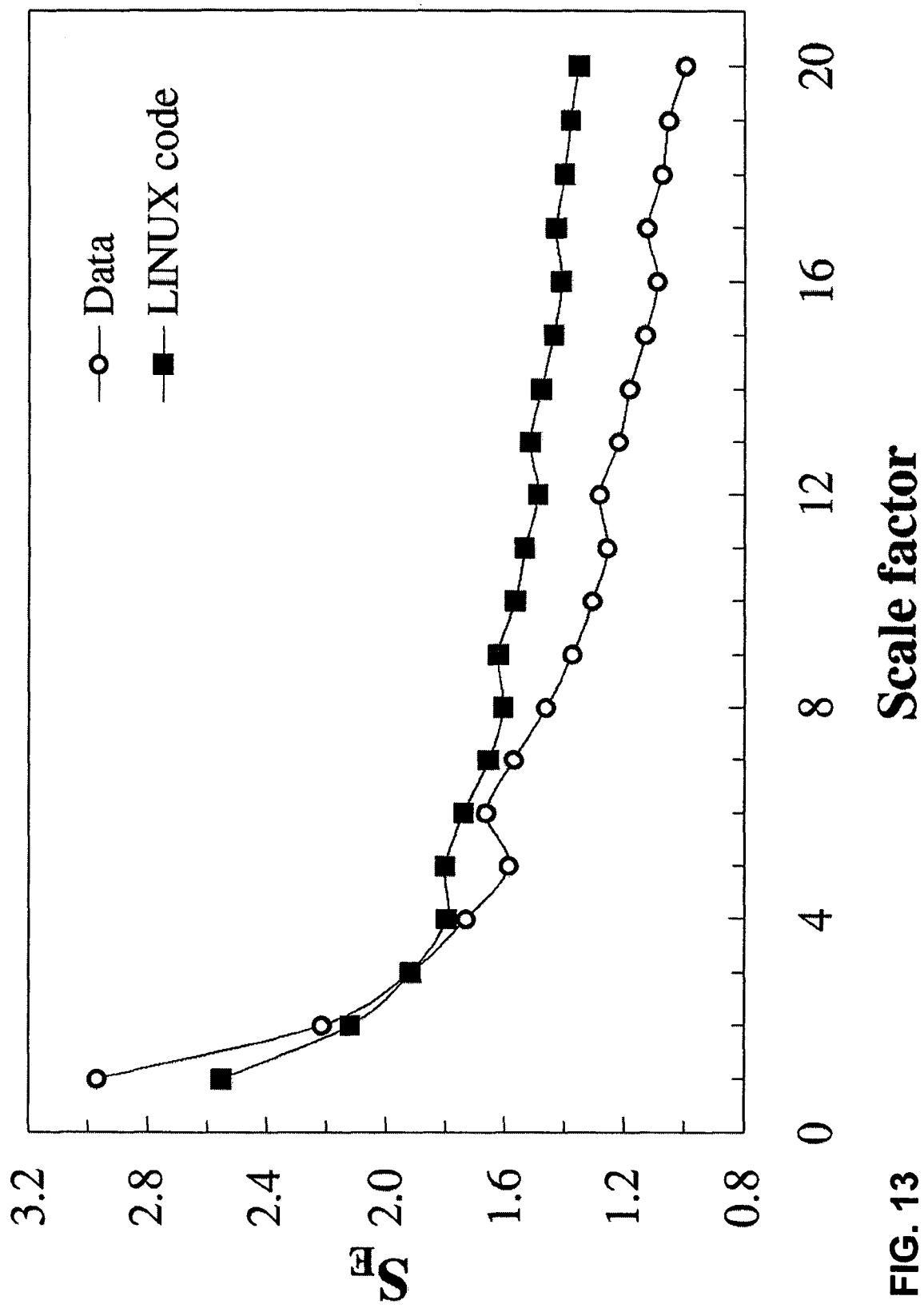

FIG. 13 illustrates an MSE analysis of binary time series derived from computer executable and computer data files.

Figure 14:
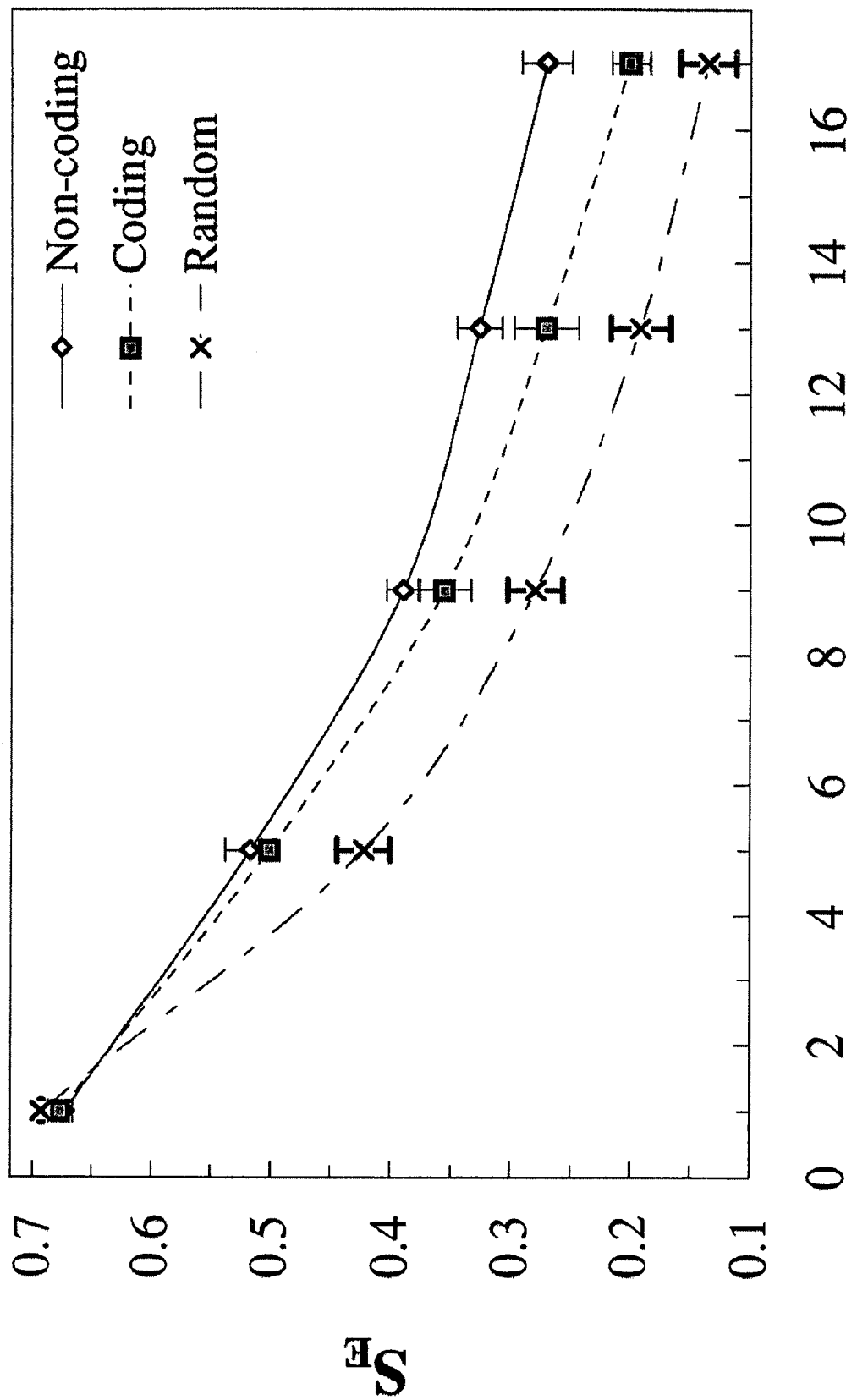

FIG. 14 illustrates an MSE analysis of human coding and noncoding DNA sequences.

Figure 15:
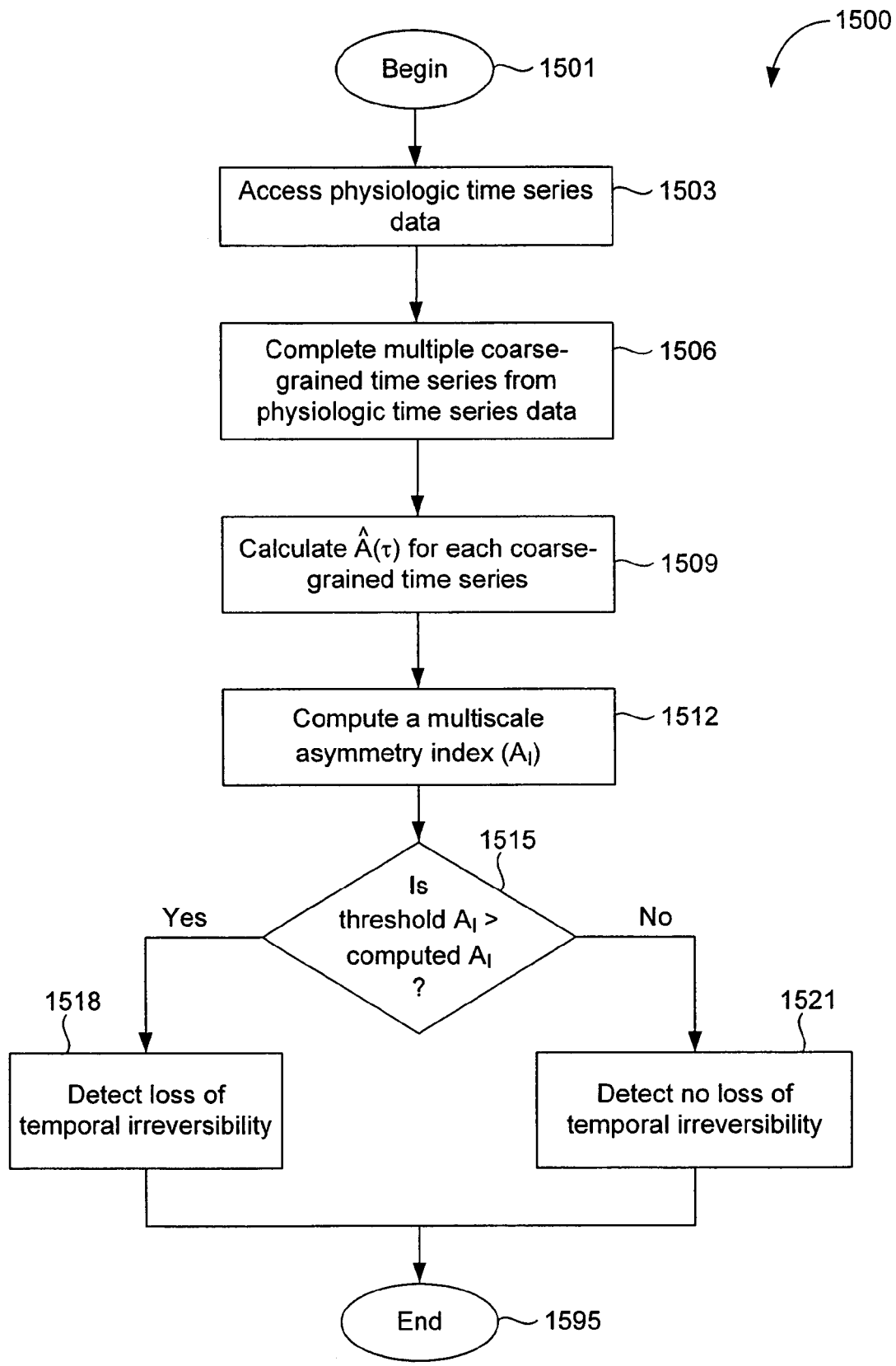

FIG. 15 illustrates a method for quantifying physiologic complexity from time asymmetry measurements.

Figure 16A:
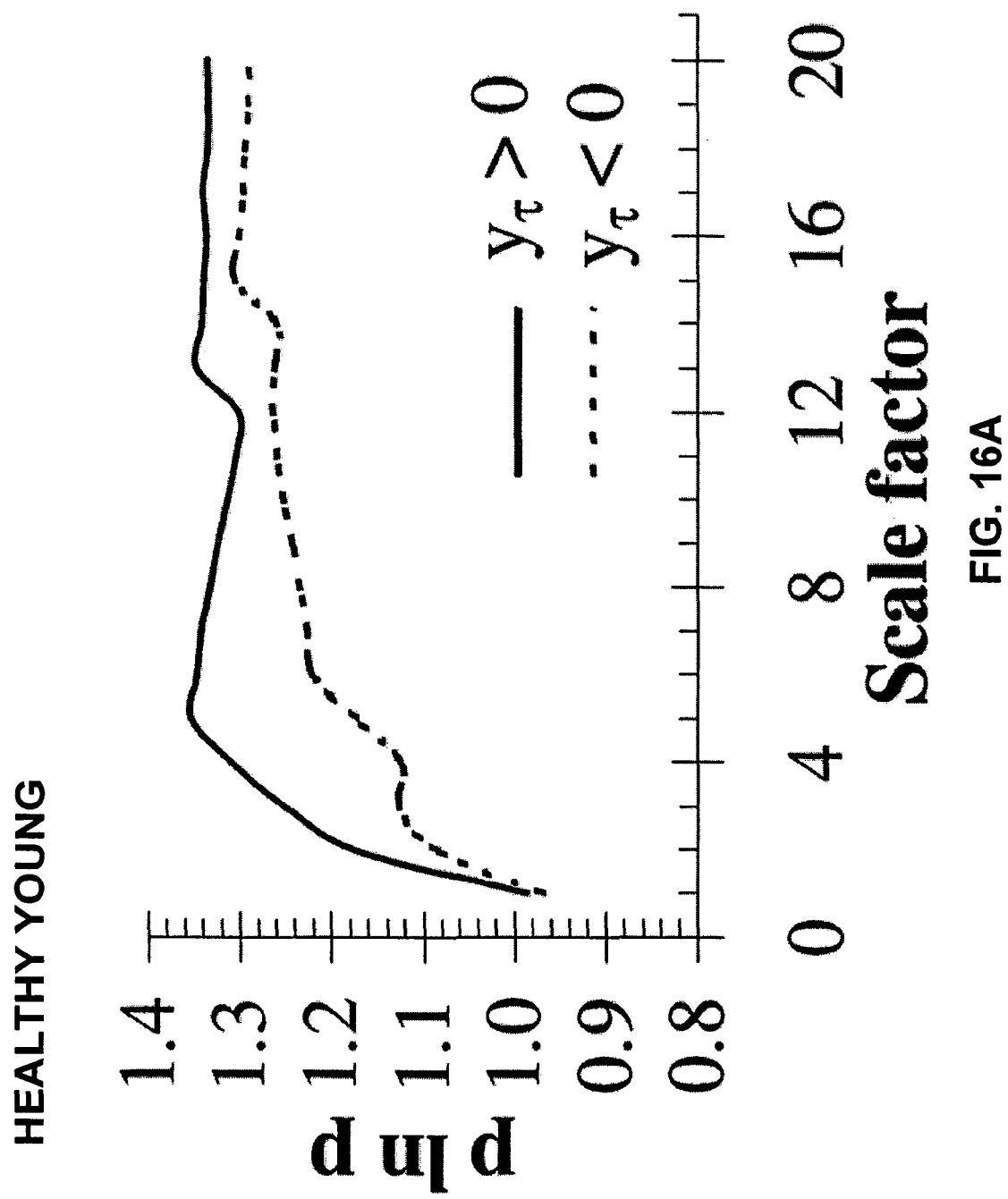
Figure 16B:
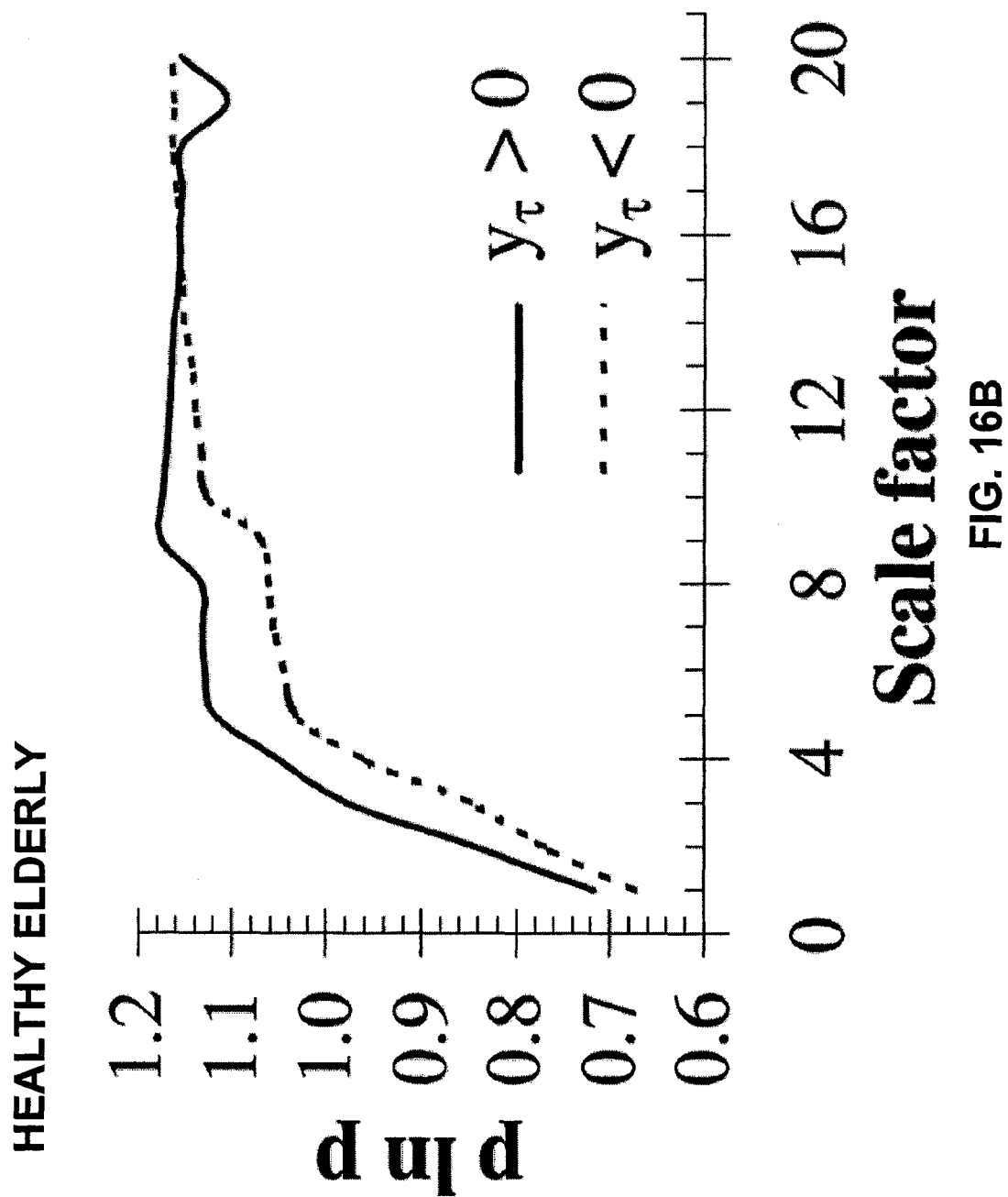
Figure 16C:
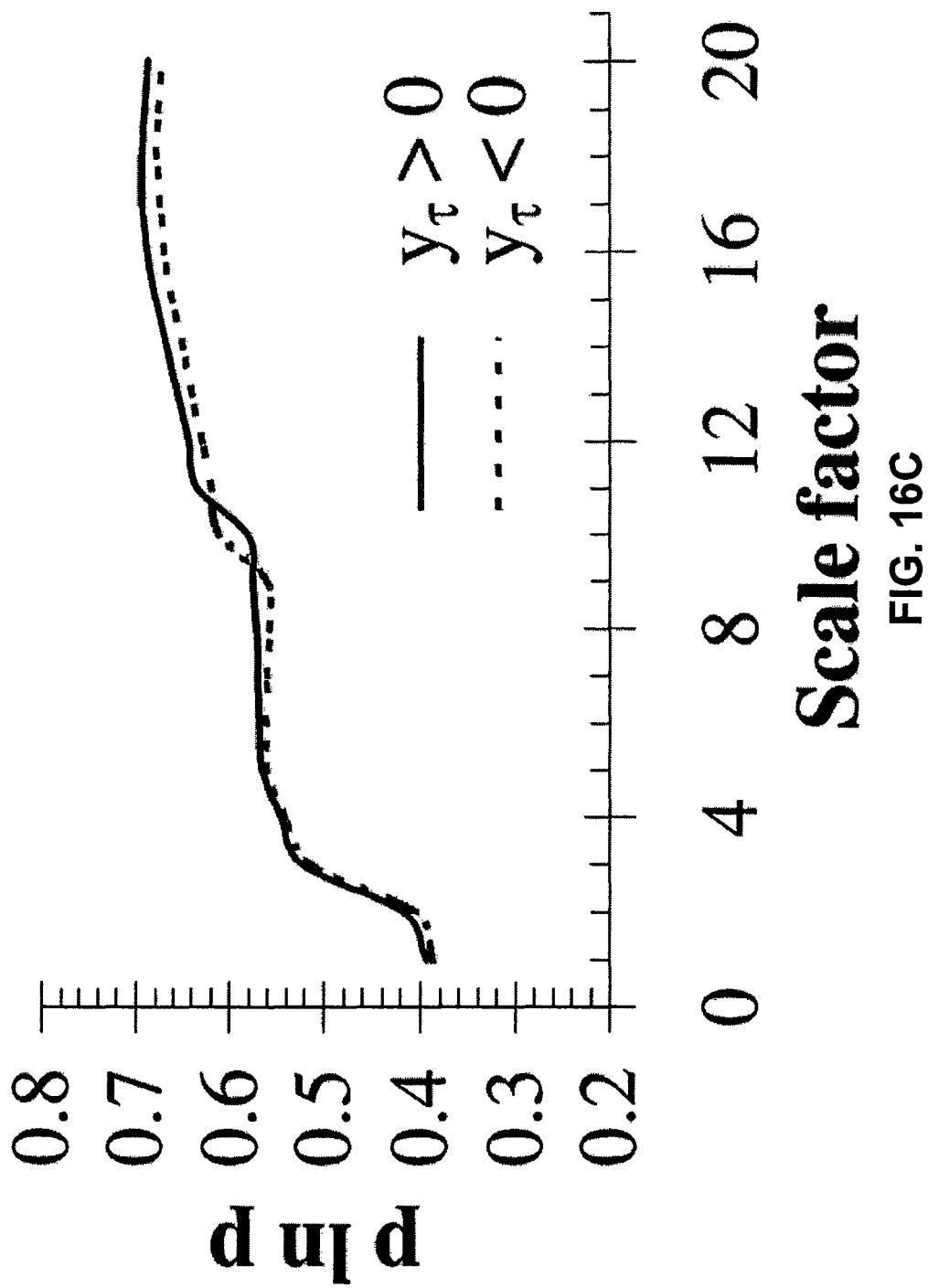
Figure 16D:
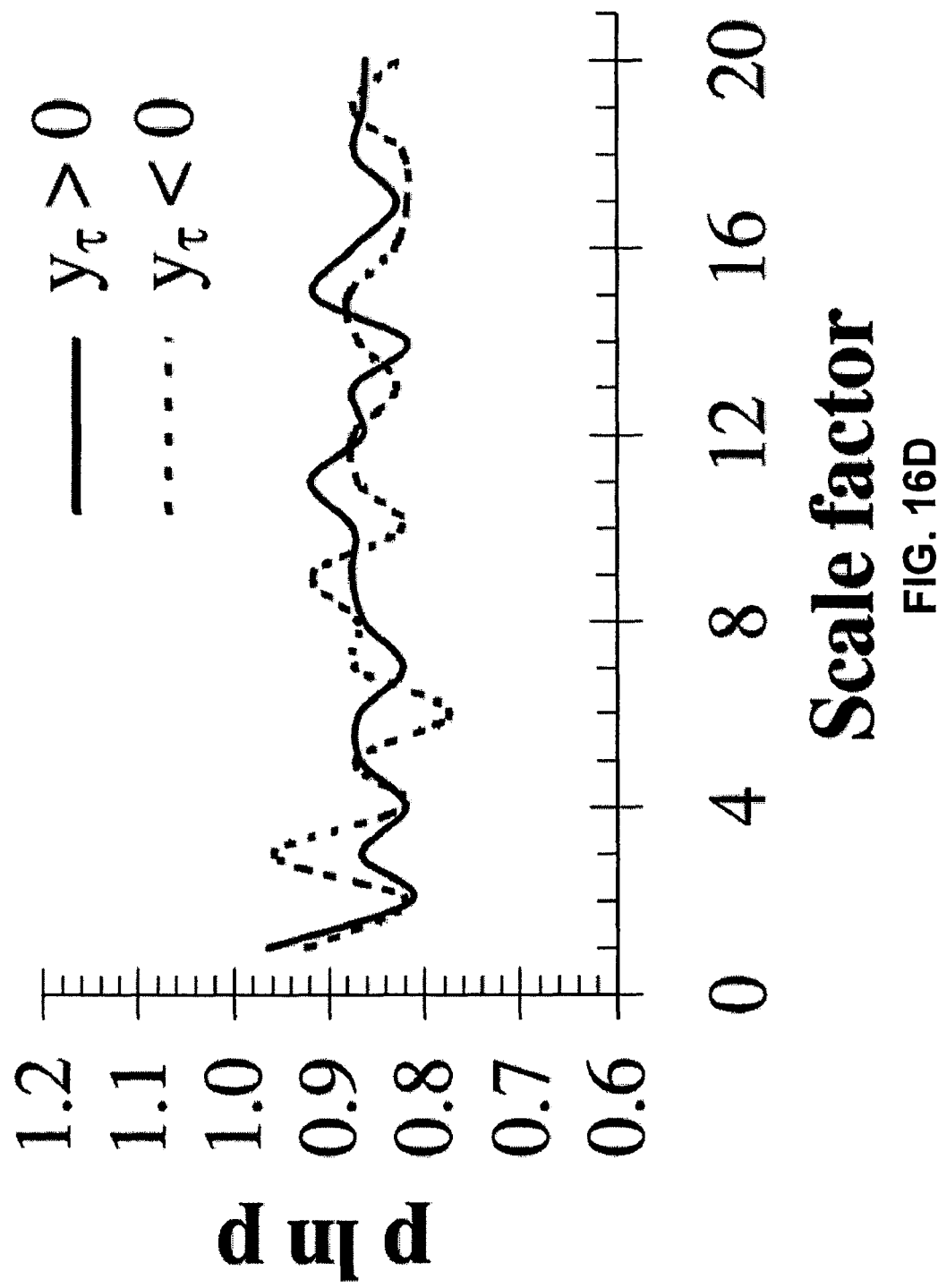
Figure 16E:
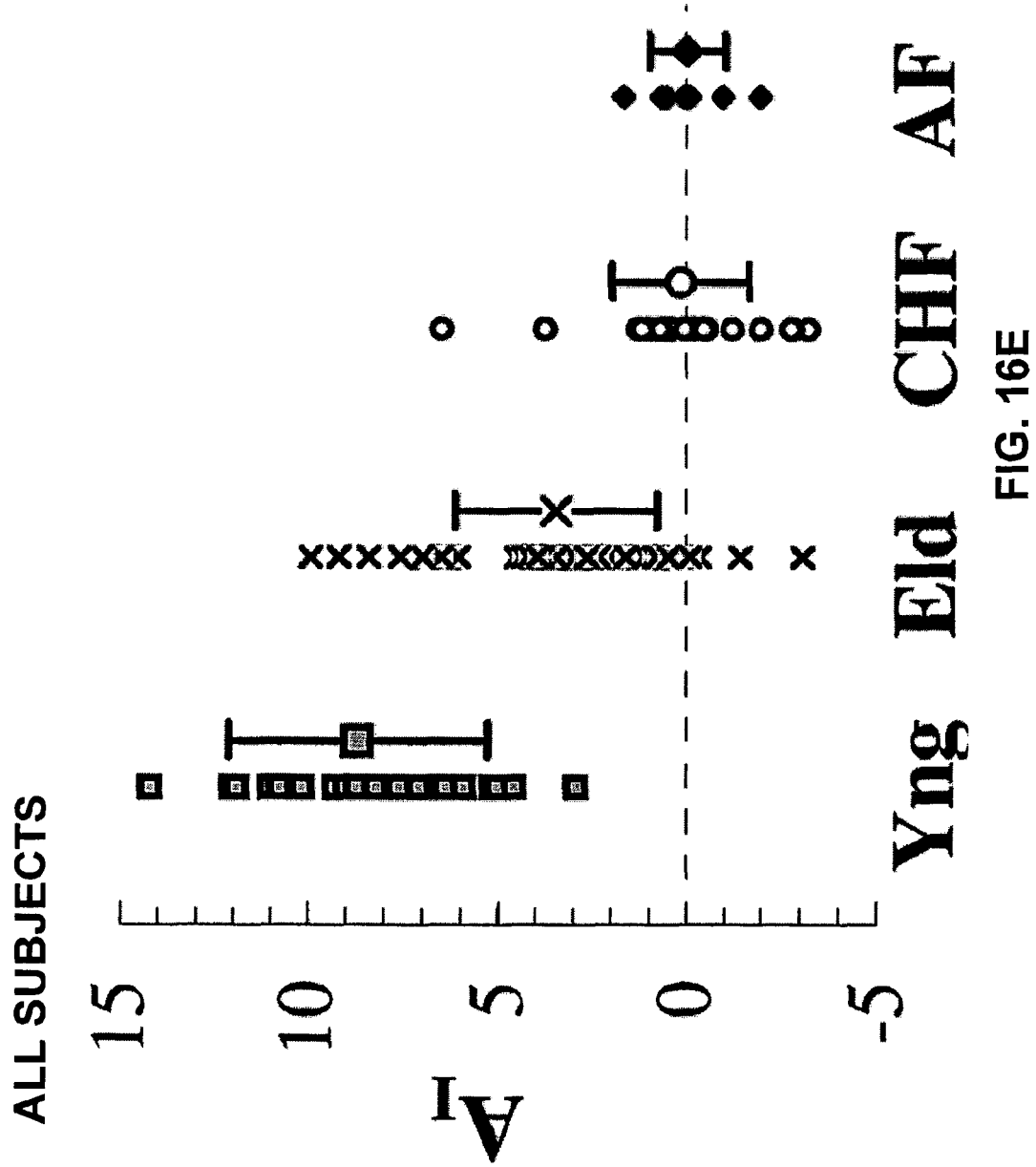

FIGS. 16A-16E illustrate a multiscale time asymmetry analysis of interbeat interval time series from representative subjects including: healthy young subjects (FIG. 16A); healthy elderly subjects (FIG. 16B); subjects with congestive heart failure (FIG. 16C); and subjects with atrial fibrillation (FIG. 16D). FIG. 16E shows the asymmetry index for a group of 26 healthy young subjects, 46 healthy elderly subjects, 43 congestive heart failure subjects and 9 subjects with atrial fibrillation.

Figure 17:
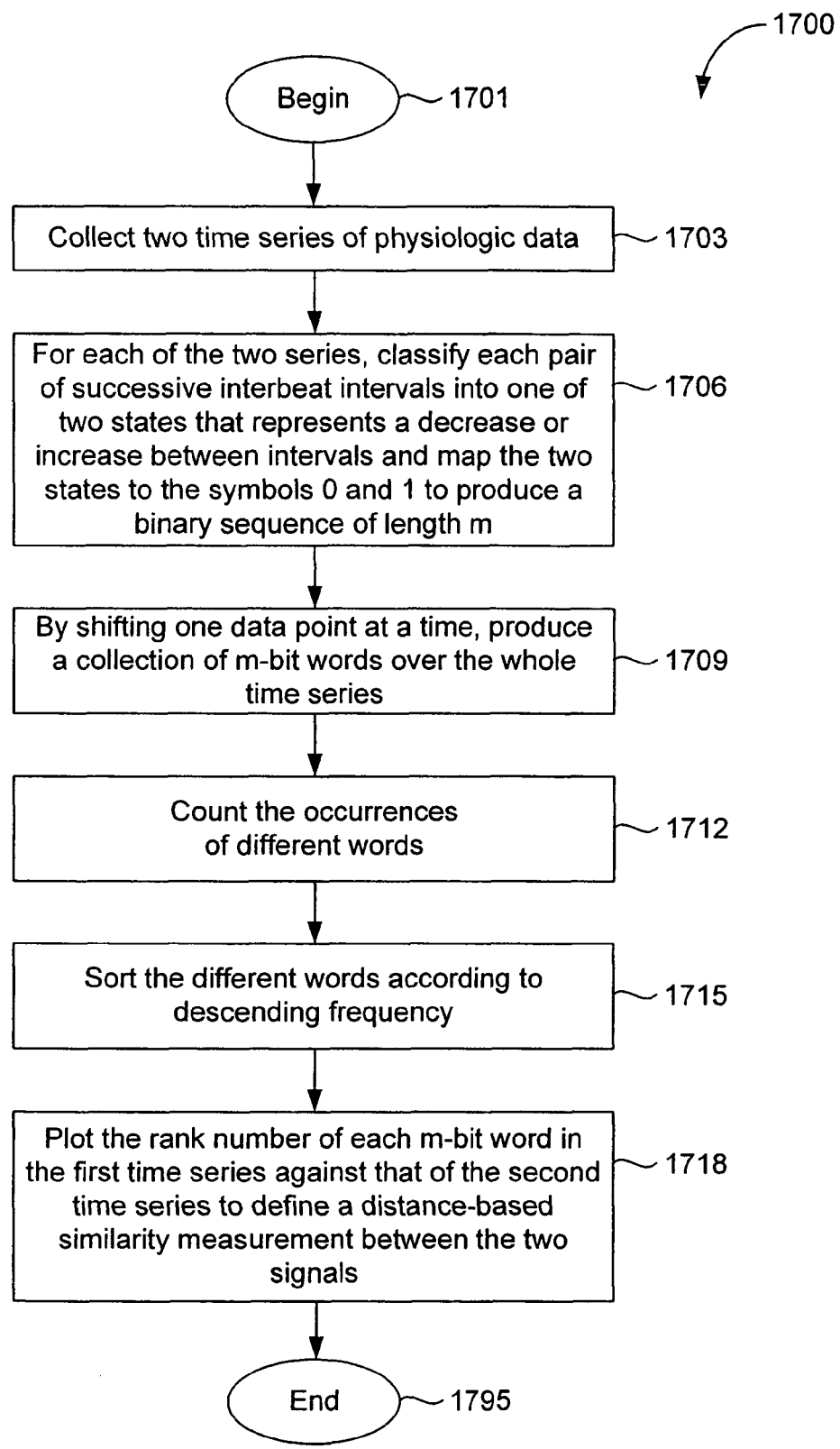

FIG. 17 illustrates a method for quantifying physiologic complexity from information-based similarity measurements.

Figure 18:
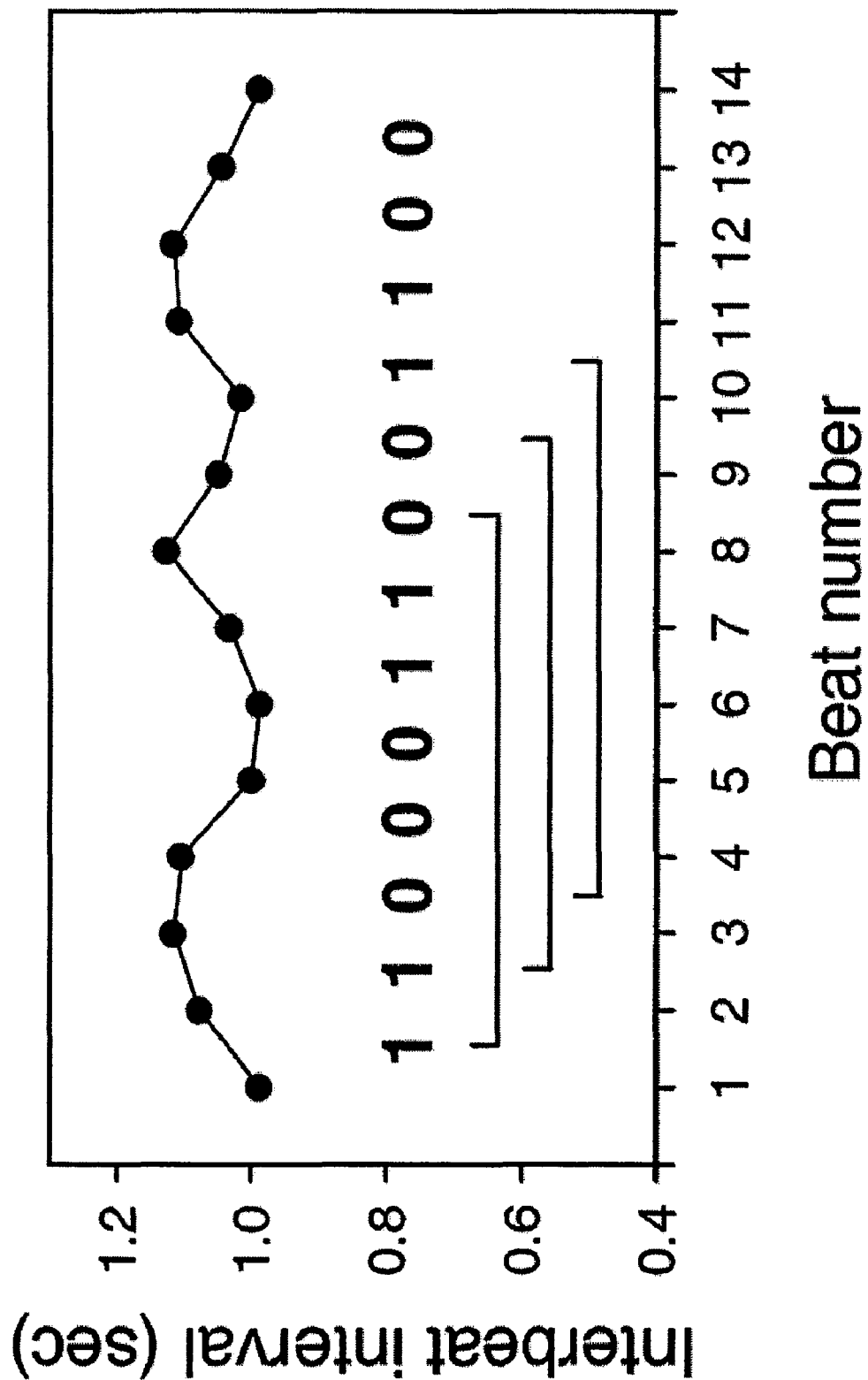

FIG. 18 illustrates a mapping procedure for 8-bit words from a time series.

Figure 19:
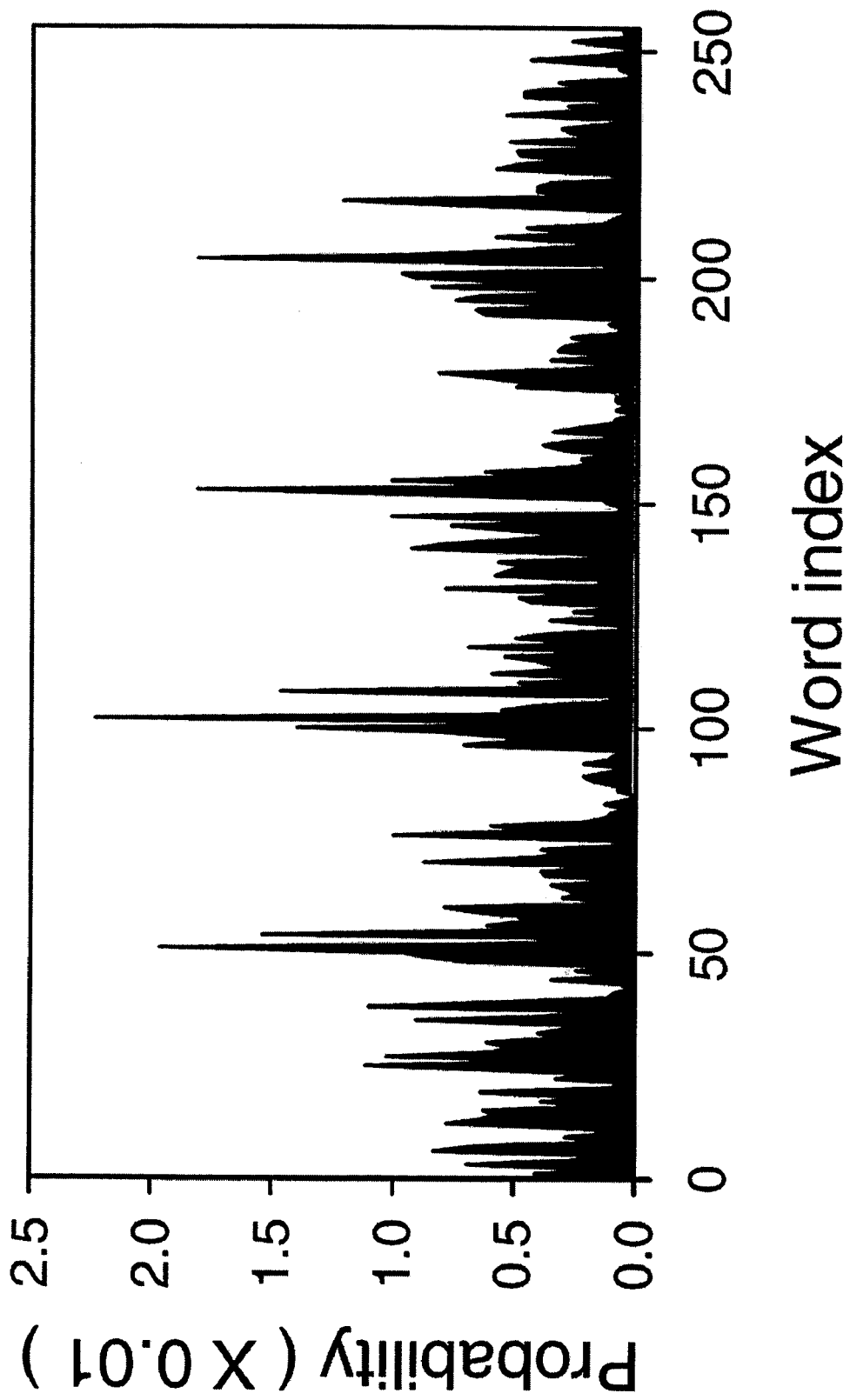
Figure 23:
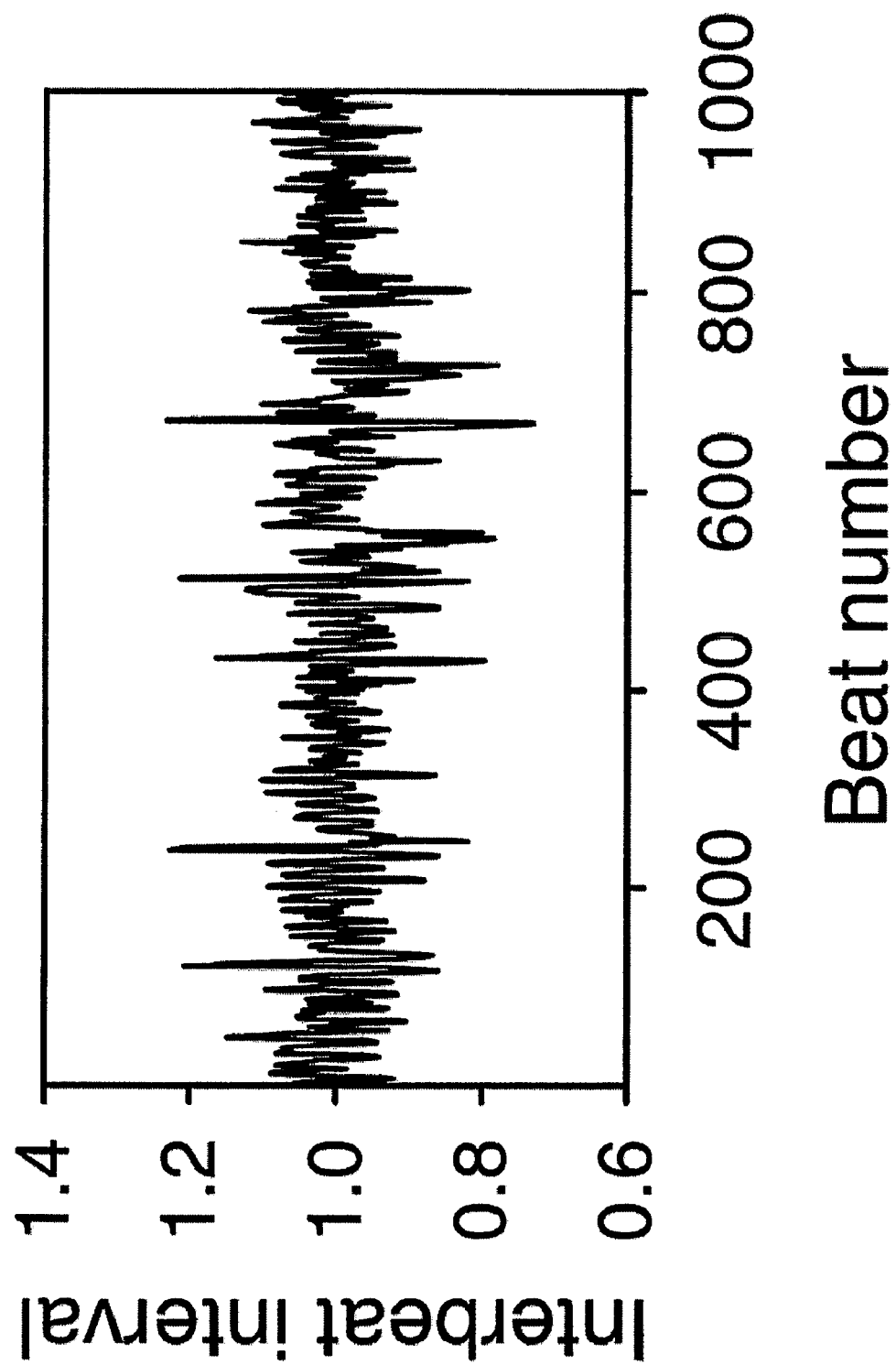

FIG. 19 illustrates a probability distribution of every 8-bit word from the time series analyzed in FIG. 23.

Figure 20:
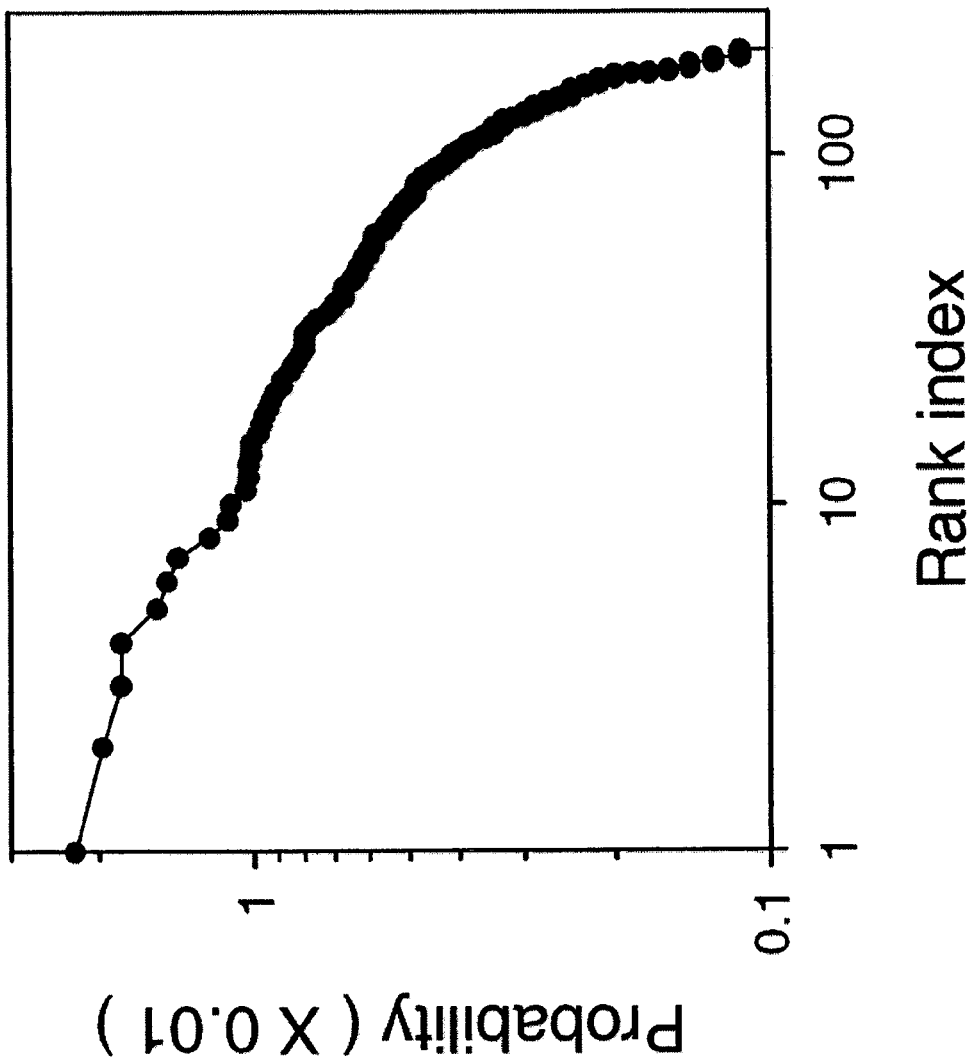

FIG. 20 illustrates a rank ordered probability plotted on a log-log scale.

Figure 21:
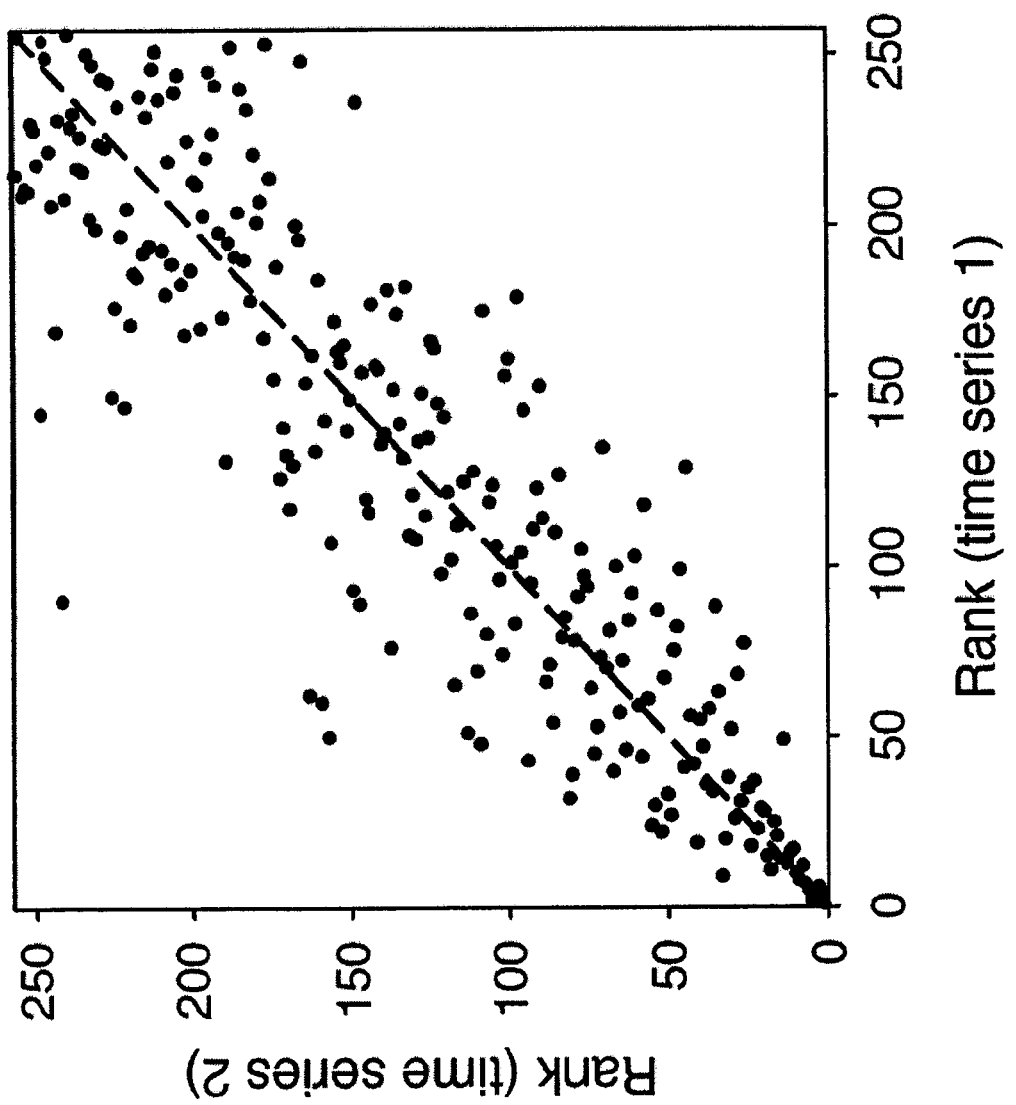

FIG. 21 illustrates a rank order comparison of two cardiac interbeat interval time series from the same subject.

Figure 22:
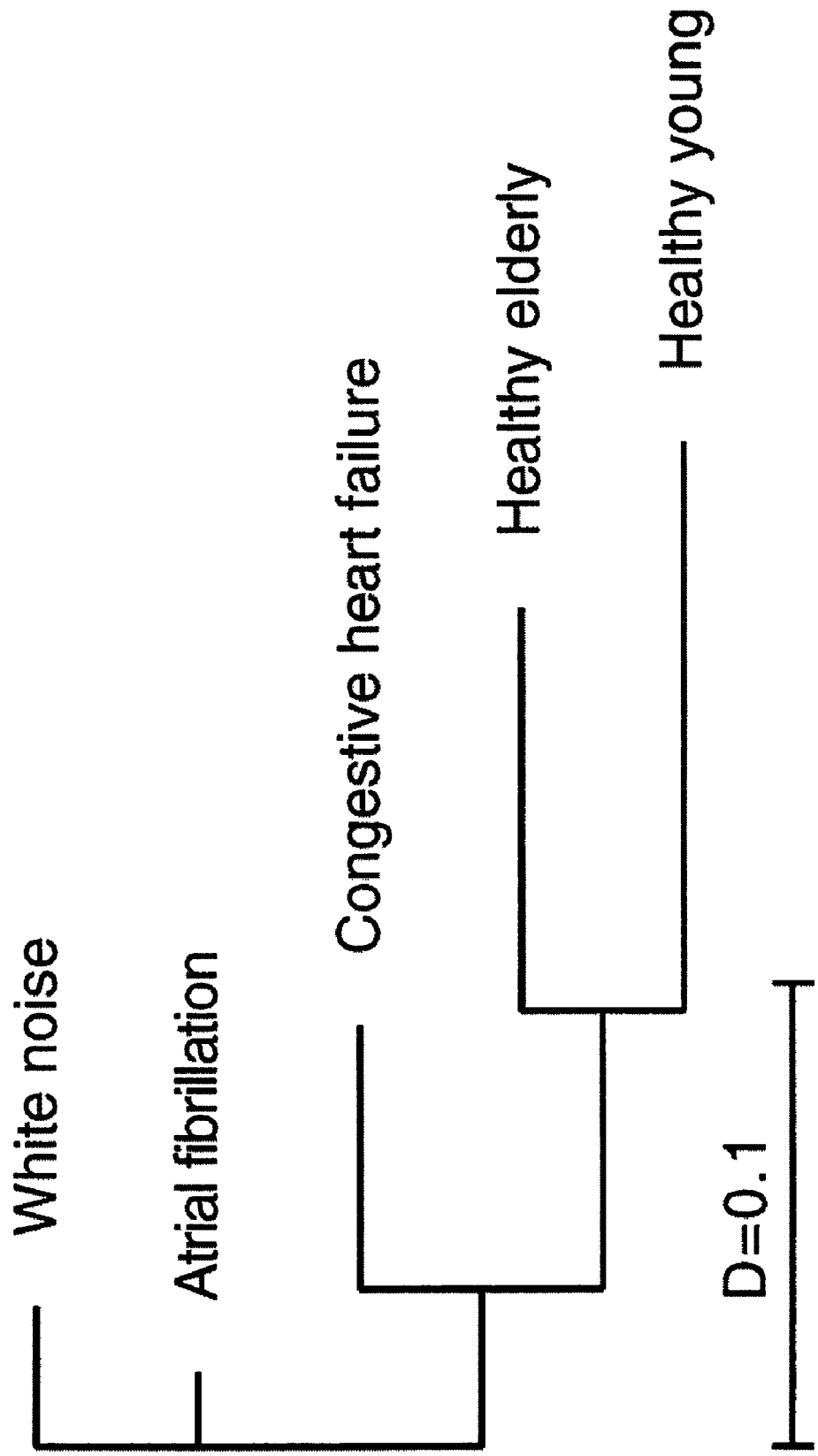

FIG. 22 illustrates a rooted phylogenic tree generated between five test groups.

FIG. 23 illustrates a heartbeat interval time series from a healthy subject.

Figure 24:
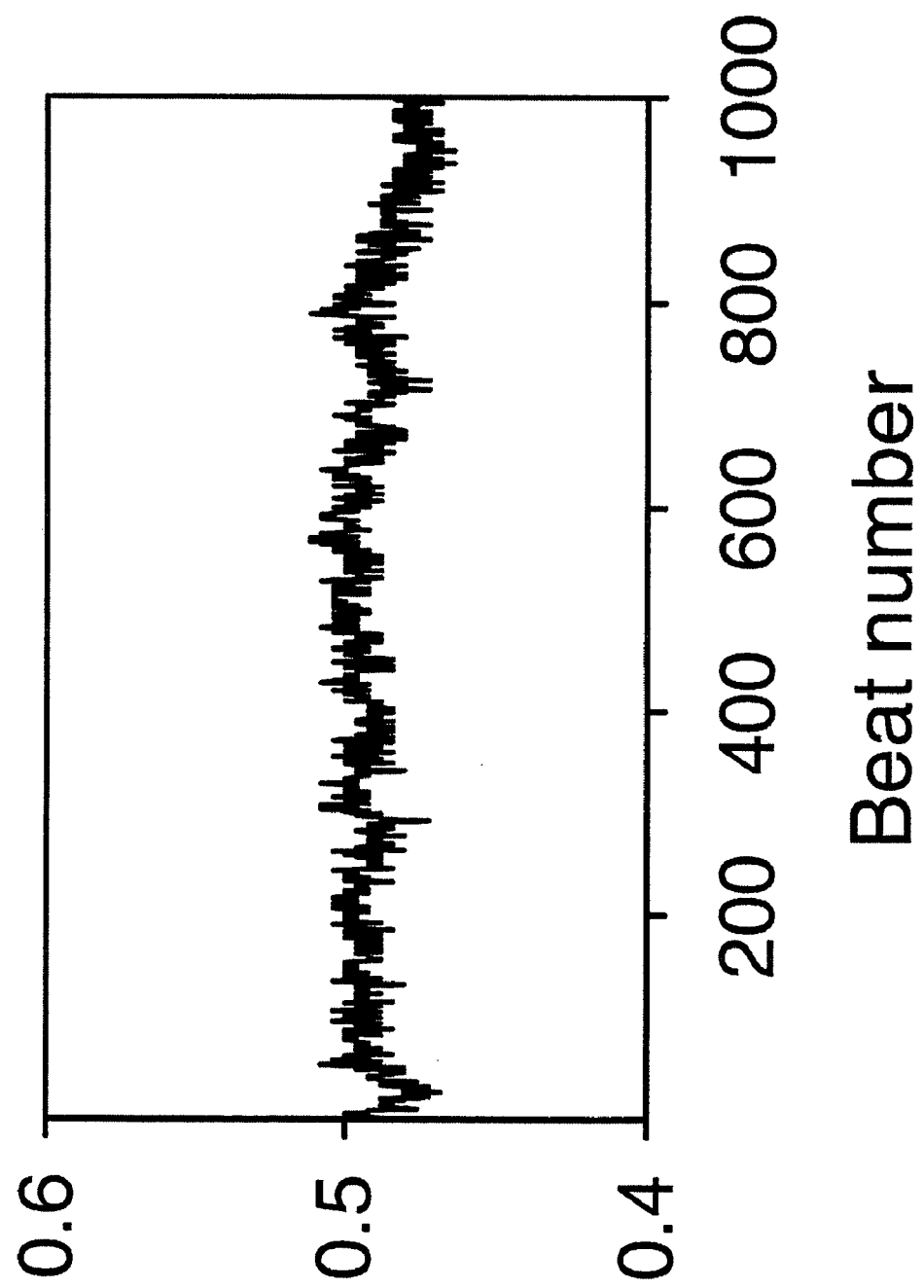

FIG. 24 illustrates a heartbeat interval time series from a subject with congestive heart failure.

Figure 25:
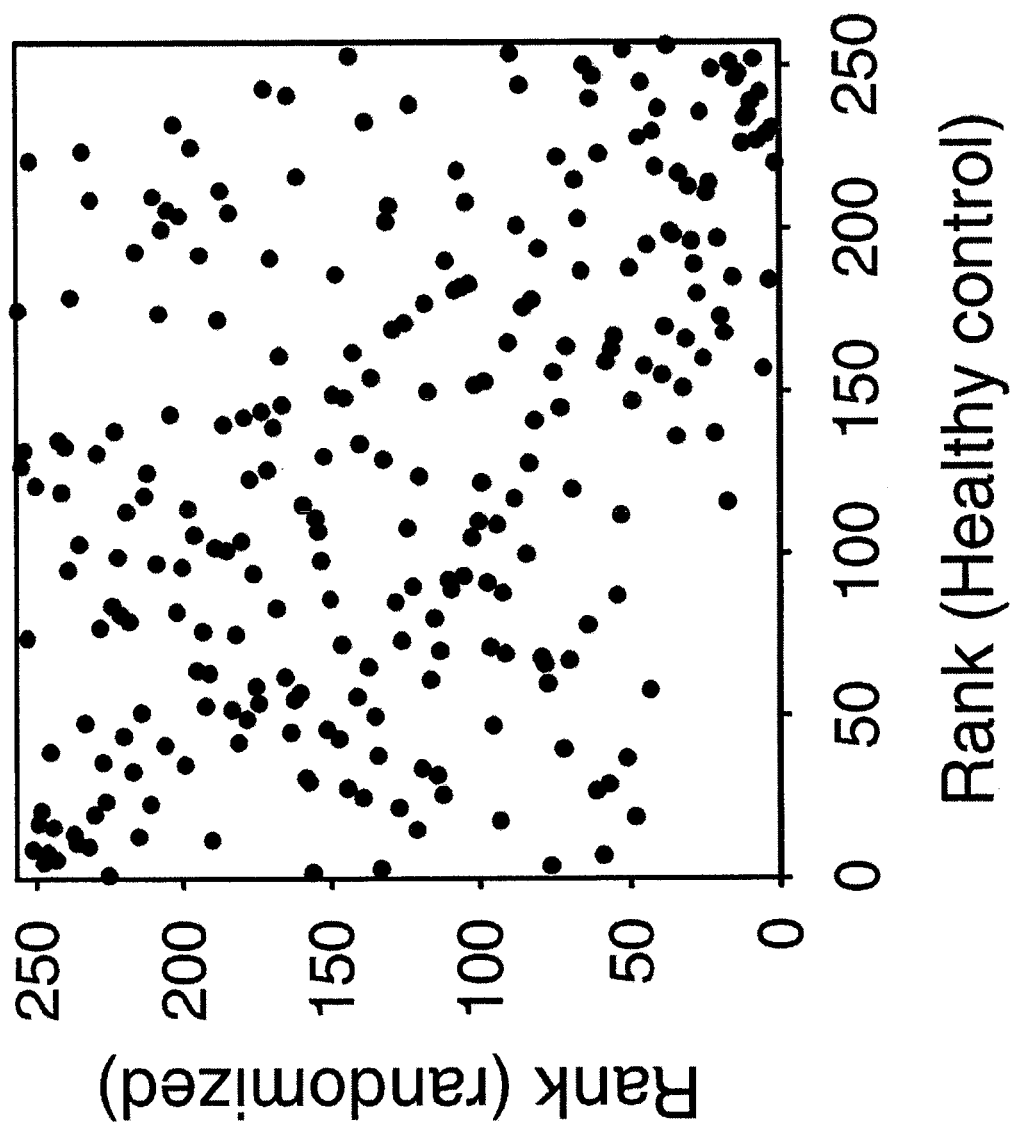

FIG. 25 illustrates a rank order comparison of the time series of FIG. 23 and its randomized surrogate.

Figure 26:
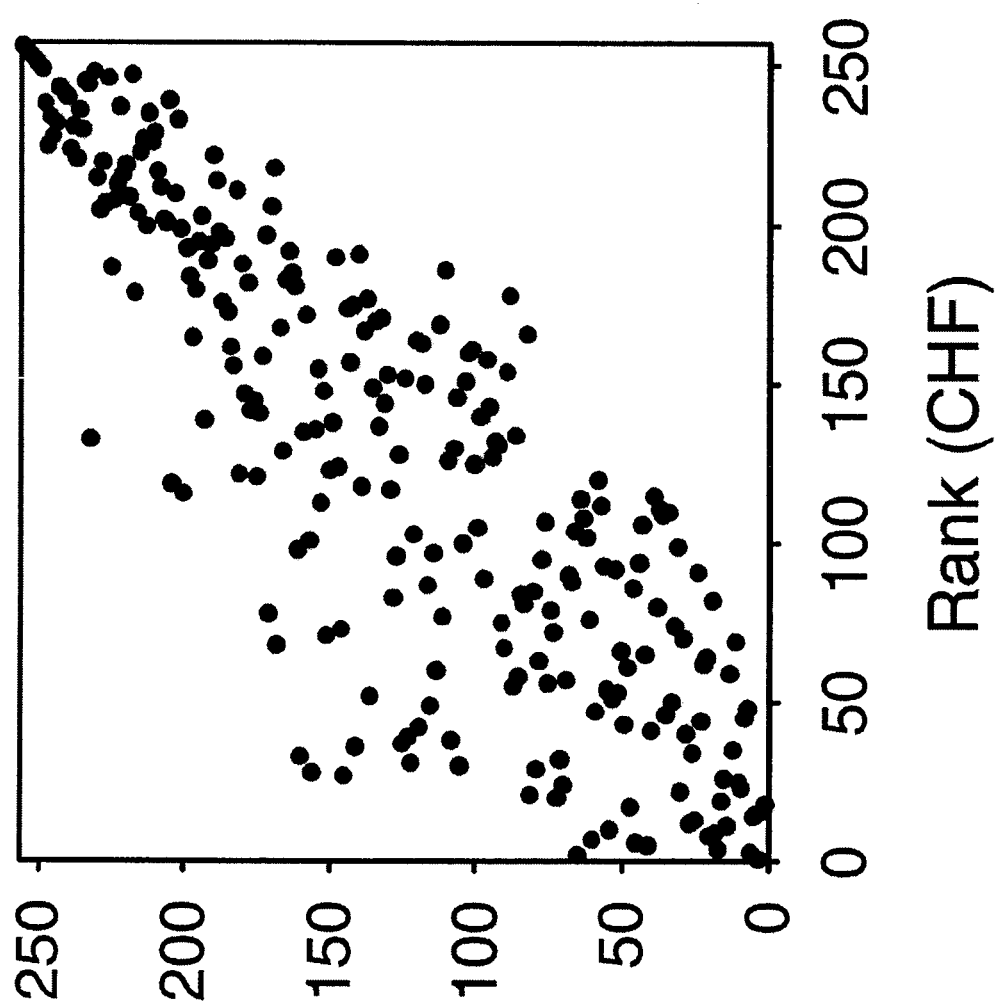

FIG. 26 illustrates a rank order comparison of the time series of FIG. 24 and its randomized surrogate.

Figure 27:
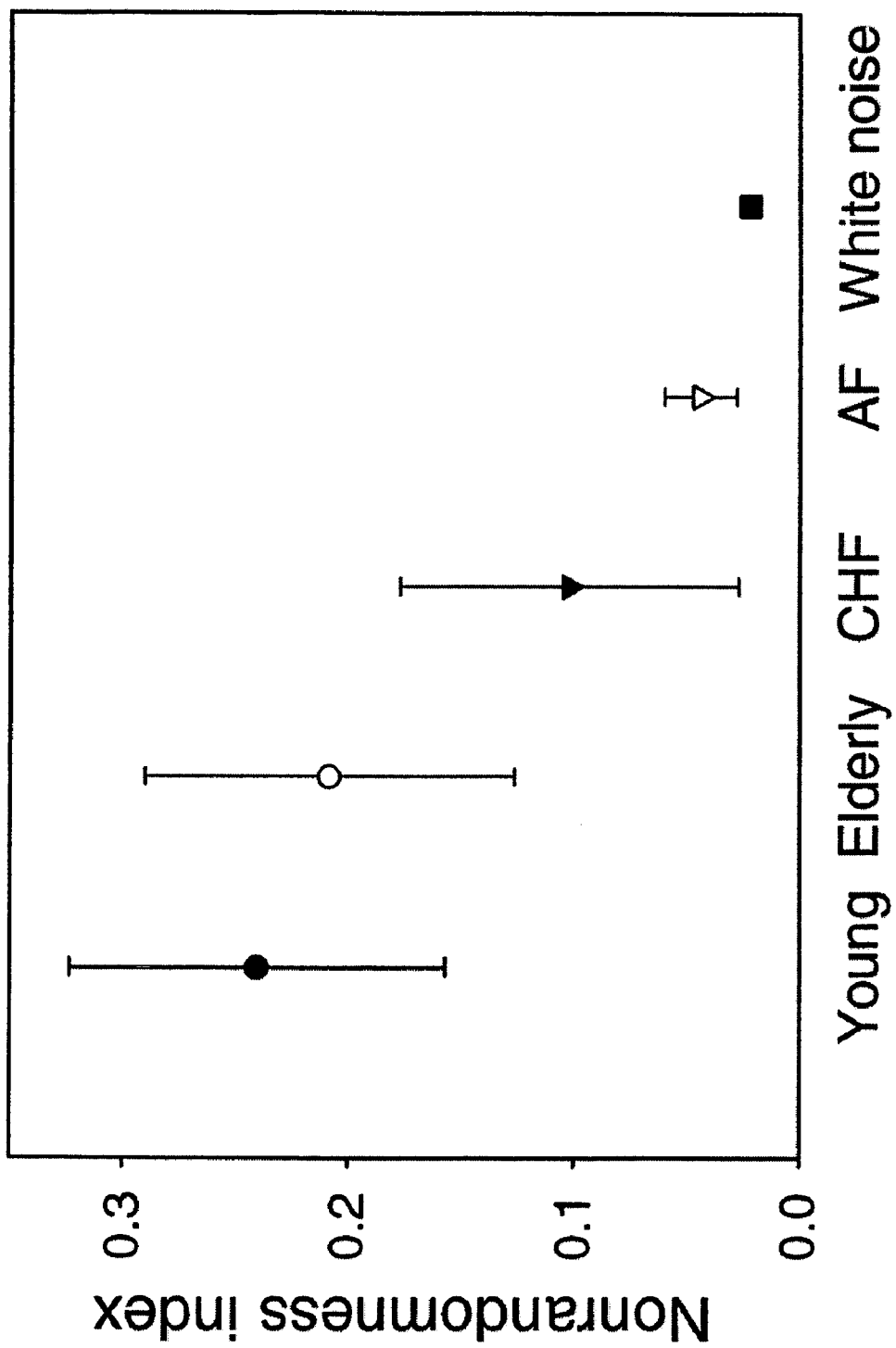

FIG. 27 illustrates nonrandomness index values of the interbeat interval time series derived from four subject groups.

Figure 28:
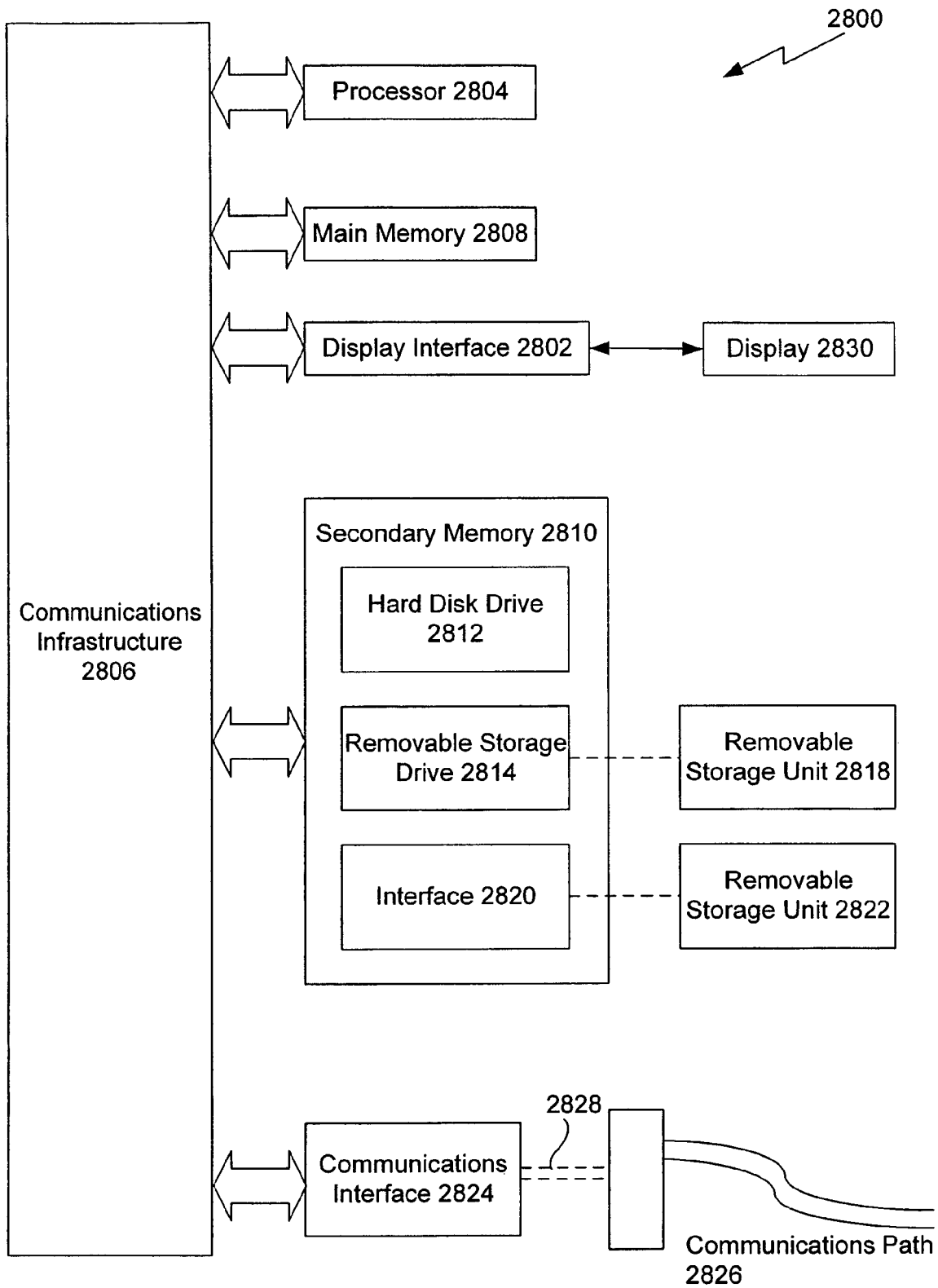

FIG. 28 illustrates an example computer system useful for implementing portions of the present invention.

DETAILED DESCRIPTION OF THE INVENTION

According to embodiments of the present invention, a method, system, and computer program product are provided to perform a quantitative analysis of the degree of physiologic complexity of an organism. Physiologic complexity is associated with the ability of living systems to adjust to an ever-changing environment, which requires integrative multiscale functionality. Under free-running conditions, a sustained decrease in complexity reflects a reduced ability of the system to function in certain dynamical regimes possibly due to decoupling or degradation of control mechanisms. Thus, physiologic complexity is a generic feature of pathologic dynamics. As such, a loss of complexity or information content is a fundamental and consistent marker of adverse effects (including pathology and age-related degenerative changes), and an increase in complexity indicates a potentially therapeutic or healthful effect.

In an embodiment, a panel of dynamical measurements quantifies different aspects of physiologic complexity and information content. The panel includes, but is not limited to, multiscale entropy (MSE), time asymmetry, and information-based similarity metrics. Each of these measurements is described in greater detail below.

By adapting methodologies from nonlinear dynamics and complexity science, the panel produces complexity and complexity related measurements based on analyses of variables that reflect system dynamics, such as cardiac interbeat interval dynamics that are readily obtained by a surface electrocardiogram. In an embodiment, the panel of dynamical measurements provides a systematic way of measuring the effects of pharmacologic and non-pharmacologic therapies and related interventions on integrated, multiscale system function. The panel provides a means for assessing efficacy and providing an early warning about potential toxicity that is not otherwise detectable by conventional assays. As discussed above, conventional assays for evaluating efficacy and toxicity fail to account for the effects on integrative physiologic function. The panel of the present invention quantifies the effects of drugs on the overall complexity of a physiologic system, and therefore is effective for monitoring and screening drug and non-pharmacologic intervention effects based on analysis of variables that reflect system dynamics.

Figure 1:
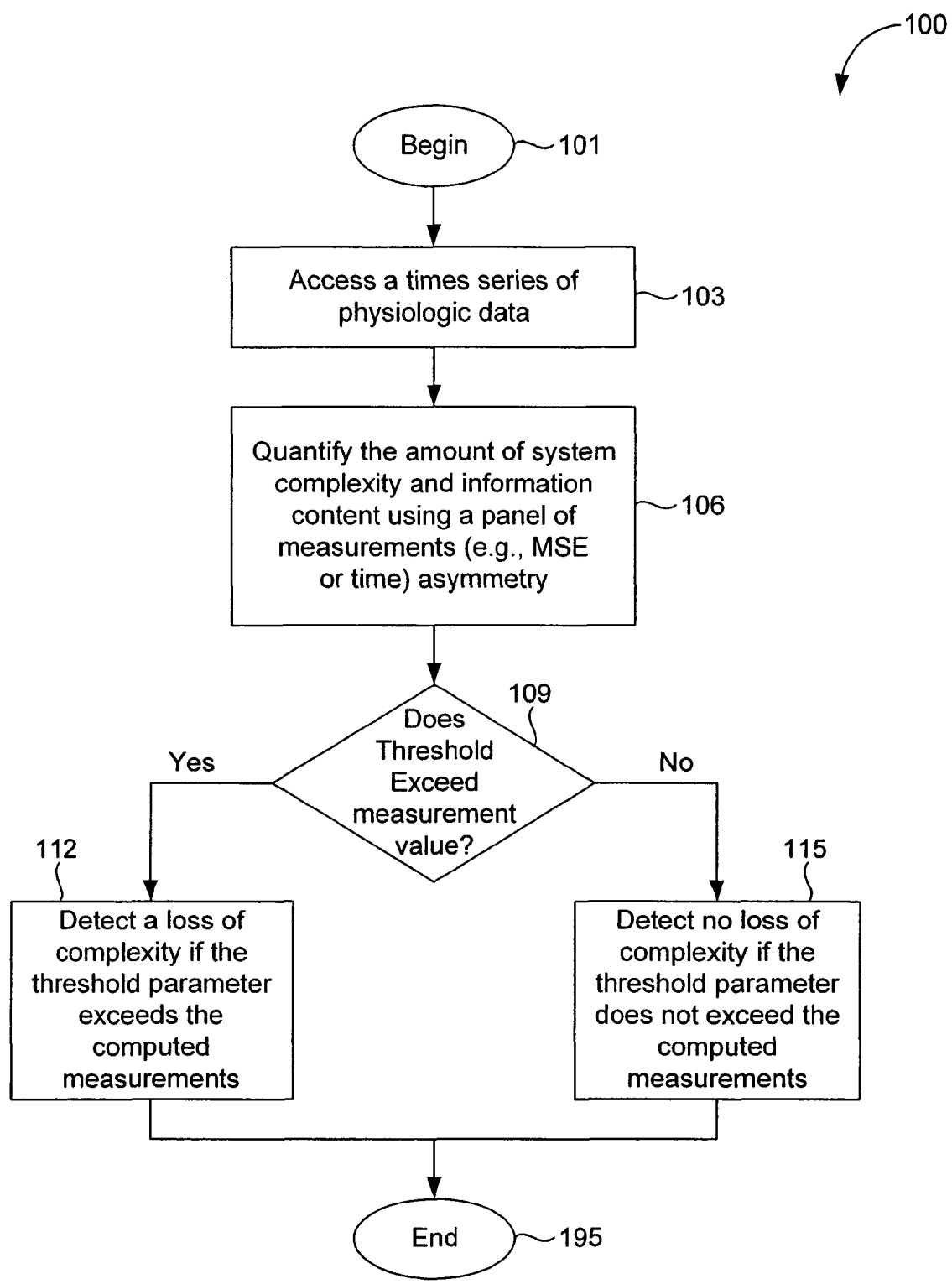
FIG. 1 illustrates a multi-panel approach for measuring complexity and information content from a subject.

Referring to FIG. 1, flowchart 100 represents the general operational flow of an embodiment of the present invention. More specifically, flowchart 100 shows an example of a control flow for measuring complexity and information content of a physiologic signal or of physiologic data from a subject (such as, a patient, test/laboratory subject, or the like) using multiscale entropy (MSE) measurements or time asymmetry measurements.

The control flow of flowchart 100 begins at step 101 and passes immediately to step 103. At step 103, a series of physiologic data is gathered from a monitoring system. For example, data can be taken from a twenty-four hour continuous electrocardiographic (ECG) Holter monitor recording of a subject. The ECG data is used to derive a cardiac interbeat (RR) interval time series. In another embodiment, an RR interval time series is acquired from another type of physiologic signal representing heart rate dynamics within a subject. Thus, the heart rate physiologic signal can be derived from, for example, ECG, blood pressure, pulse Doppler flow (e.g., sensed via ultrasound recording), ECG signal from another electrical signal (e.g., electroencephalographic (EEG)), or the like.

In another embodiment, other types of non-invasive and invasive measurements can be used in conjunction with or in lieu of a heart rate physiologic data. For example, the physiologic data can include a respiratory signal, an electroencephalographic (EEG) signal, a neuromuscular signal, or the like.

At step 106, the ECG and/or other non-invasive or invasive measurements are processed to quantify the system's complexity and information content. In an embodiment, a panel of complexity-based measurements is applied to quantify the system complexity and information content. In this embodiment, the panel includes, but is not limited to, MSE and time asymmetry measurements. To quantify the complexity, one or more of the panel measurements are applied. Each of these measurements is described in greater detail below.

At step 109, the computed complexity-based measurement(s) are compared to a threshold parameter(s). The threshold parameter(s) represent base values or values computed from a normal or healthy subject. The threshold parameter(s) are described in greater detail below.

If the threshold parameter(s) exceed the computed measurement(s), control passes to step 112, and loss of complexity is detected. Otherwise, control passes to step 115, and no loss of complexity is detected. A gain in complexity is determined if the computed measurement(s) exceed the threshold parameter(s). Afterwards, the control flow ends as indicated at step 195.

As discussed, the present invention can be used to quantity the effects of drug and non-pharmacologic intervention. As such, interventions that enhance system complexity (as detected at step 115) are associated with therapeutic effects, and those interventions that degrade system complexity (as detected at step 112) are associated with adverse effects.

Accordingly, the present invention can be used in preclinical animal and Phase 1-3 clinical design, development and testing of pharmacologic agents to help assess therapeutic efficacy and toxicity. The present invention can also be used in high throughput testing of drugs and other non-pharmacologic interventions to screen for new agents with salutary integrated physiologic effects that might not be detected by conventional screening. The present invention can also be used to assess approved pharmacologic agents and other non-pharmacologic interventions to detect potential toxicities not identified in animal and Phase 1-3 trials by the United States Food and Drug Administration (FDA) or other governmental agencies.

The approach has been tested on three pharmacologic agents, namely encainide, flecainide and moricizine, using data from a subset comprising 30 subjects of an open-access database from the historic Cardiac Arrhythmia Suppression Trial (CAST) study. This database is available at the website: http://www.physionet.org/physiobank/database/crisdb/.
These three cardiac antiarrhythmic agents were shown, unexpectedly in the original trial, to increase mortality. Re-analysis of the pre- and post-drug Holter monitor data from this study using complexity-based measurements of the present invention identifies a loss of complexity in heart rate dynamics after administration for all three agents, thereby providing direct evidence for increased risk of adverse future outcomes. The finding of a loss of system complexity with any drug is a major "red flag" since it suggests loss of system adaptability and functionality. The present invention provides a way to screen new cardiac antiarrhythmic agents (and, indeed all other drugs) for such "hidden" toxicity.

Multiscale Entropy (MSE) Analysis of Physiologic Signals

As discussed, the present invention provides a panel of dynamical measurements that quantifies different aspects of physiologic complexity and information content. In one embodiment, the panel of dynamical measurements includes, but is not limited to, MSE measurements and time asymmetry measurements. The first methodology, the MSE approach, is effective for investigating complexity in physiologic signals and other series that have correlations at multiple time scales. As described herein, the MSE approach is utilized to characterize the fluctuations of a human heartbeat under physiologic and pathologic conditions. However, other types of physiologic data series can be used, including but not limited to, respiratory signals, brain waves, or the like.

Conventional methods quantify the degree of regularity of a time series on a single scale by evaluating the appearance of repetitive patterns. However, there is no straightforward correspondence between regularity, which can be measured by entropy-based algorithms, and complexity. Intuitively, complexity is associated with "meaningful structural richness," which, in contrast to the outputs of random phenomena, exhibits relatively higher regularity. (See P. Grassberger in *Information Dynamics*, edited by H. Atmanspacher et al., p 15, Plenum Press, NY, 1991, which is incorporated herein by reference). Entropy-based measures, such as the entropy rate and the Kolmogorov complexity, grow monotonically with the degree of randomness. Therefore, these measures assign the highest values to uncorrelated random signals (i.e., white noise), which are highly unpredictable but not structurally "complex," and, at a global level, admit a very simple description.

The MSE approach integrates information about the degree of irregularity of a time series in multiple scales. The MSE approach is based on the hypothesis that the outputs of more complex dynamical systems likely present structures with higher information content in multiple scales than those from less complex systems. The MSE method consistently reveals that correlated random signals (e.g., 1/f noise time series) are more complex than uncorrelated random signals (e.g., white noise time series). These results are consistent with the presence of long-range correlations in 1/f noise time series but not in white noise time series. In contrast, the analysis of the same time series with single scale-based entropy algorithms may lead to misleading results as higher entropy values are assigned to white noise than to 1/f noise time series.

When applied to physiologic time series, conventional entropy-based algorithms can lead also to misleading results. For example, they assign higher entropy values to certain pathologic cardiac rhythms that generate erratic outputs than to healthy cardiac rhythms that are exquisitely regulated by multiple interacting control mechanisms.

The present invention addresses this longstanding problem and is predicated on the following hypotheses: i) the complexity of a biological system reflects its ability to adapt and function in an ever-changing environment; ii) biological systems need to operate across multiple spatial and temporal scales, and hence their complexity is also multi-scaled; and iii) a wide class of disease states as well as aging which reduce the adaptive capacity of the individual, appear to degrade the information carried by output variables. Thus, a loss of complexity is a generic feature of pathologic dynamics. Accordingly, the MSE approach of the present invention computes a complexity measurement that focuses on quantifying the information expressed by the physiologic dynamics over multiple spatial and temporal scales.

Due to the interrelationship of entropy and scale, which is incorporated in the MSE approach, the results are consistent with the consideration that both completely ordered and completely random signals are not really complex. Compared to conventional complexity measures, the MSE approach has the advantage of being applicable to both physiologic and physical signals of finite length.

Figure 2:
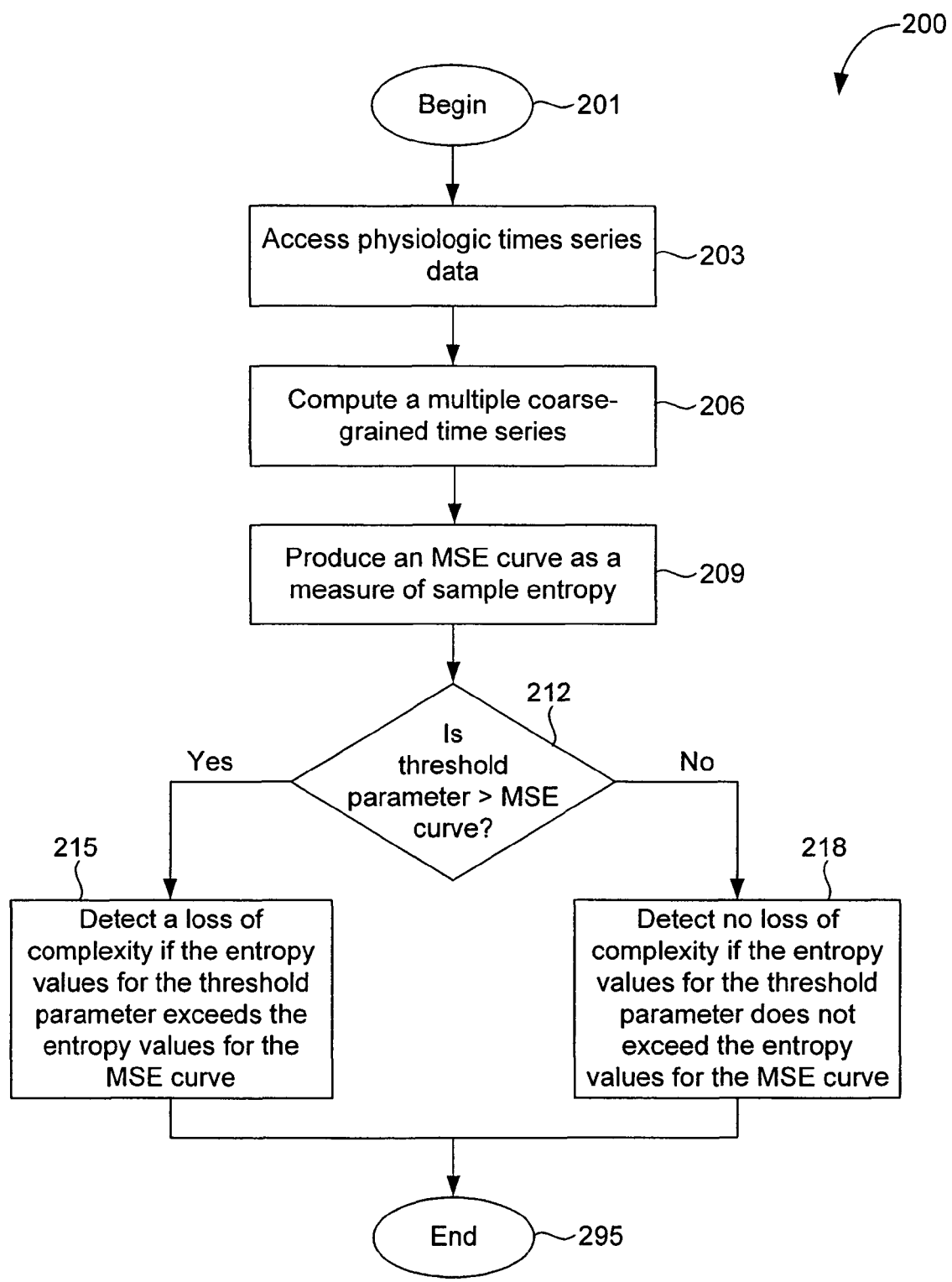
FIG. 2 illustrates quantifying physiologic complexity from MSE measurements.

Referring to FIG. 2, flowchart 200 represents the general operational flow of an embodiment of the present invention. More specifically, flowchart 200 shows an example of a control flow for quantifying physiologic complexity from MSE measurements.

The control flow of flowchart 200 begins at step 201 and passes immediately to step 203. At step 203, a series of physiologic data is gathered from non-invasive and/or invasive measurements taken from a subject. For example, data can be taken from a twenty-four hour continuous ECG Holter monitor recording, and used to derive an RR interval time series.

At step 206, the physiologic time series data is processed to compute multiple coarse-grained time series. For instance, given a one-dimensional discrete time series $\{x_1, \ldots, x_i, \ldots, x_N\}$ that represents the physiologic time series data, consecutive coarse-grained time series $\{y^{(\tau)}\}$ can be constructed that corresponds to the scale factor $\tau$. To compute the coarse-grained time series, the original time series is divided into non-overlapping windows of length $\tau$, and the data points inside each window are averaged. In an embodiment, each element of the coarse-grained time series is calculated according to the equation:

$$y_j^{(\tau)} = \frac{1}{\tau} \sum_{i=(j-1)\tau+1}^{j\tau} x_i, \ 1 \le j \le N/\tau$$

Figure 3:
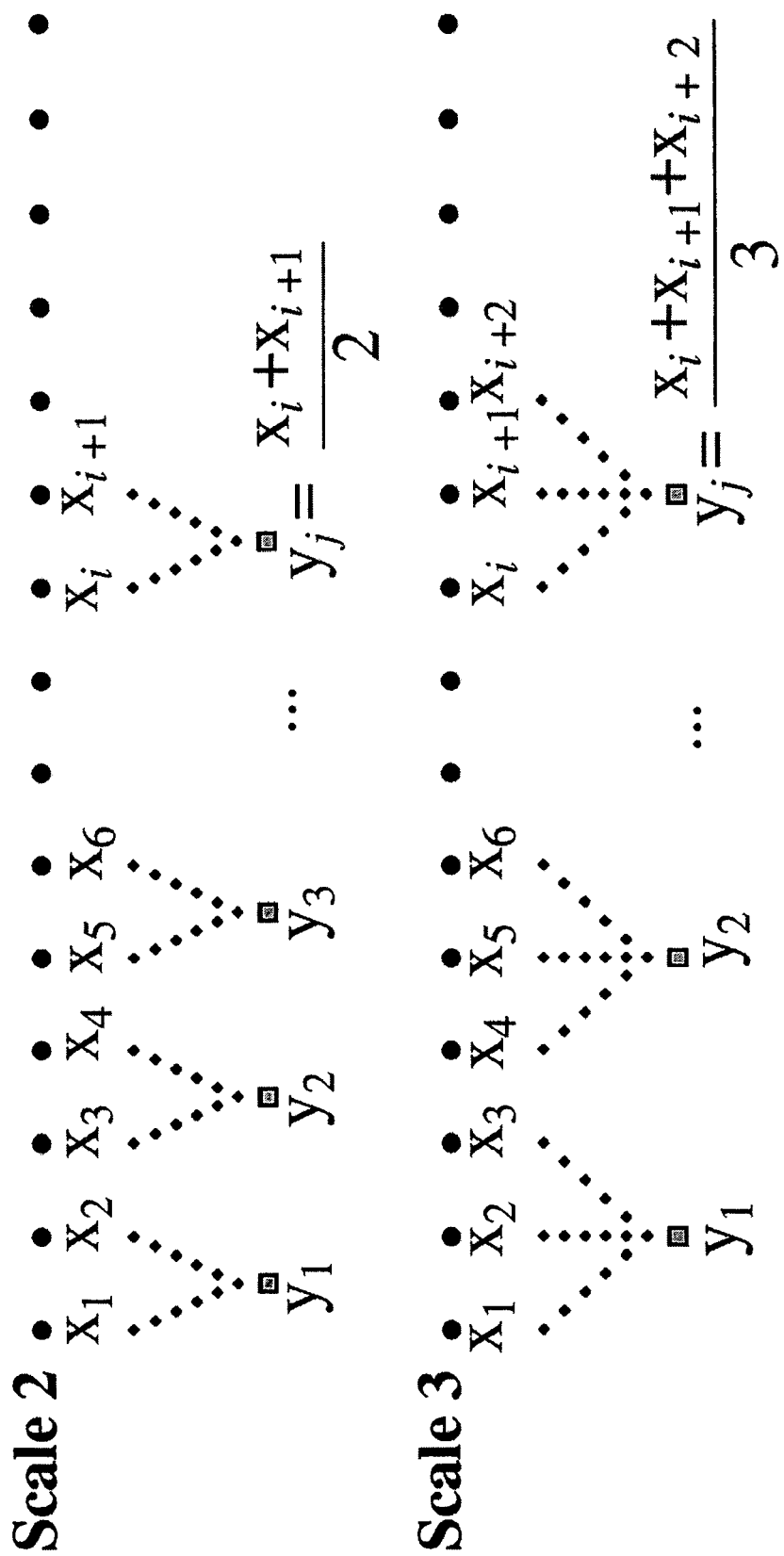
FIG. 3 illustrates coarse-graining a data series for scales 2 and 3.

The length of each coarse-grained time series is equal to the length of the original time series divided by the scale factor $\tau$. For scale one, the time series $\{y^{(1)}\}$ is simply the original time series, or N/$\tau$. Similarly, the length of the time series is N/2 for scale 2, the length is N/3 for scale 3, and so forth. FIG. 3 illustrates the coarse-graining process for scales 2 and 3, according to an embodiment of the present invention.

At step 209, the sample entropy statistic is used to calculate entropy for each coarse-grained time series plotted as a function of the scale factor $\tau$. The plotted function is herein referred to as an MSE curve.

At step 212, the plotted MSE curve is compared to a template MSE curve representative of a normal or healthy subject or of the subject being studied before the initiation of the therapy or in an earlier state of the disease.

If, for a given range of scales, the values of the entropy and/or of parameters derived from the template MSE curve are higher than those from the plotted MSE curve, control passes to step 215, and loss of complexity is detected for all scales within that range. Otherwise, control passes to step 218. If, for a given range of scales, the values of the entropy and/or of parameters derived from the computed MSE curve are higher than those from the template MSE curve, an increase in complexity is determined.

A monotonic decrease of the entropy values indicates that the original signal contains information only in the smallest scale, in which case the time series has very low complexity. Afterwards, the control flow ends as indicated at step 295.

In the discussion above of steps 209 and 212, an MSE curve is plotted and compared to a template MSE curve. While curve plotting provides a visual mechanism for comparing data and observing similarities and/or differences in the underlying data, a person skilled in the art will recognize that such plotting is optional. For example, in an alternate embodiment, a computer can be used to compare the MSE data without requiring plotting.

As discussed above, the MSE approach can be used to quantify the effects of drug and non-pharmacologic intervention. As such, interventions that enhance system complexity (as detected at step 218) are associated with therapeutic effects, and those interventions that degrade system complexity (as detected at step 215) are associated with adverse effects.

As discussed above, entropy values defining the MSE curves are calculated using an entropy statistic called sample entropy (see Richman et al. Am. J. Physiol. 2000, 278: J239-H249, which is incorporated herein by reference), according to the equation:

$$SE(m, r, N) = \ln \frac{\sum_{i=1}^{N-m} n_i^m}{\sum_{i=1}^{N-m} n_i^{m+1}}$$

Figure 4:
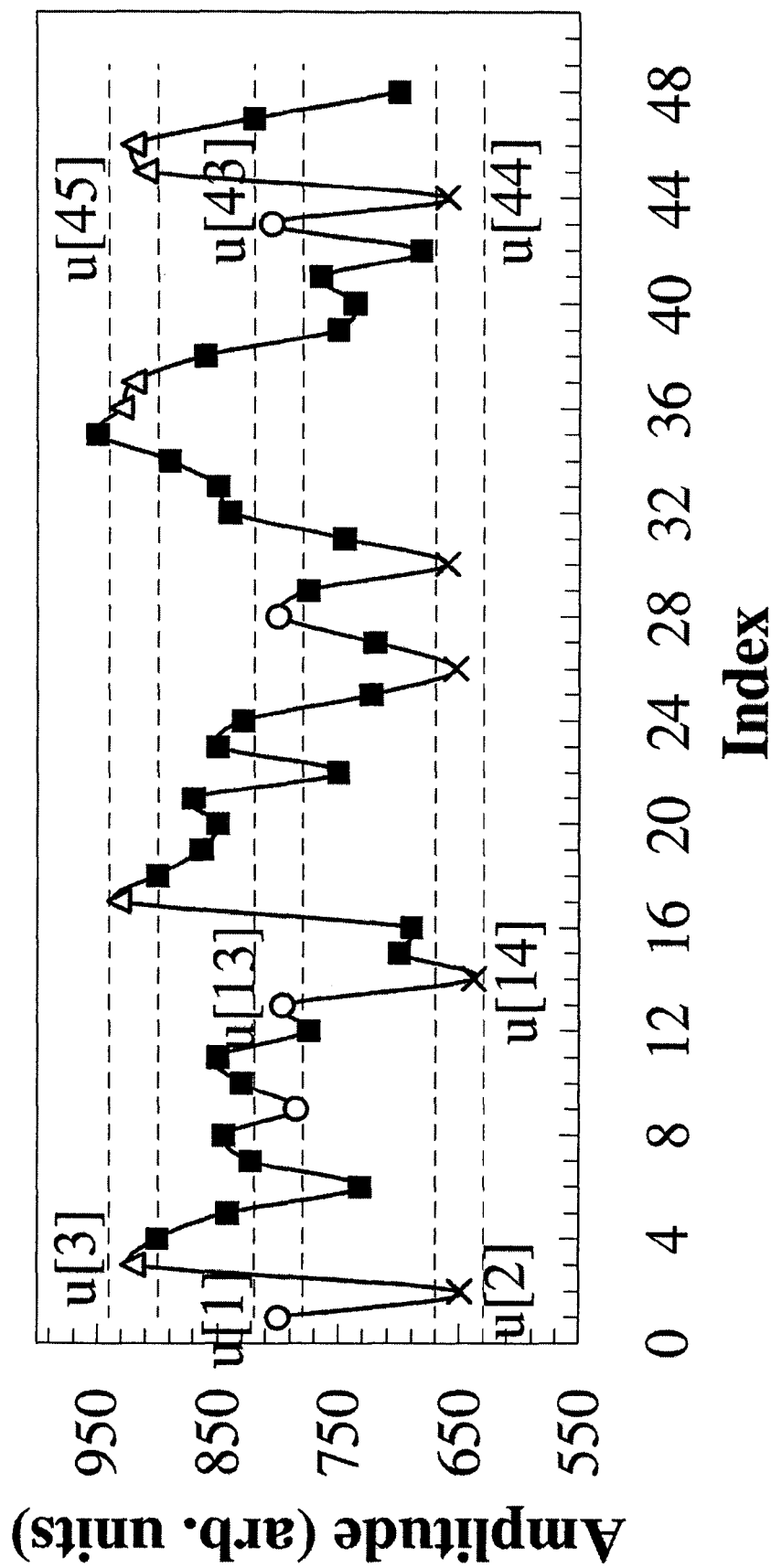
FIG. 4 illustrates a calculation of sample entropy.

Sample entropy is equal to the negative of the natural logarithm of the conditional probability that sequences close to each other for "m" consecutive data points would also be close to each other when one more point is added to each sequence. FIG. 4 illustrates the calculation of sample entropy, according to an embodiment of the present invention. A simulated time series u[1], . . . , u[N] is shown to illustrate the procedure for calculating sample entropy for the case in which the pattern length "m" is 2, and "r" is a given positive real value. Typically, r is a given positive real value that is chosen to be between 10% and 20% of the sample deviation of the time series. Dotted horizontal lines around data points u[1], u[2] and u[3] represent u[1]±r, u[2]±r, and u[3]±r, respectively. Two data values match each other, that is, they are indistinguishable, if the absolute difference between them is ≦r. The symbol "o" is used to represent data points that match the data point u[1]. Similarly, the symbols "x" and "Δ" are used to represent data points u[2] and u[3], respectively.

Consider the 2-component "o-x" template sequence (u[1], u[2]) and the 3-component "o-x-Δ" (u[1], u[2], u[3]) template sequence. For the segment shown in FIG. 4, there are two "o-x" sequences, (u[13], u[14]) and (u[43], u[44]), that match the template sequence (u[1], u[2]) but only one "o-x-Δ" sequence that matches the template sequence (u[1], u[2], u[3]). Therefore, in this case, the number of sequences matching the 2-component template sequences is two and the number of sequences matching the 3-component template sequence is one. These calculations are repeated for the next 2-component and 3-component template sequence, which are, (u[2], u[3]) and (u[2], u[3], u[4]), respectively. The numbers of sequences that match each of the 2-component and 3-component template sequences are again counted and added to the previous values. This procedure is then repeated for all other possible template sequences, (u[3], u[4], u[5]), . . . , (u[N−2], u[N−1], u[N]), to determine the ratio between the total number of 2-component template matches and the total number of 3-component template matches. The sample entropy, therefore, is the natural logarithm of this ratio and reflects the probability that sequences that match each other for the first two data points will also match for the next point.

The MSE approach of the present invention has been tested on cardiac interbeat (RR) interval time series derived from twenty-four hour continuous ECG Holter monitor recordings of (a) healthy subjects, (b) subjects with congestive heart failure (a life-threatening condition), and (c) subjects with atrial fibrillation (a major cardiac arrhythmia). This data is available at http://physionet.org.

The data for the normal control group were obtained from a twenty-four hour Holter monitor recordings of seventy-two healthy subjects (including thirty-five men and thirty-seven women, aged 54.6±16.2 years (mean±SD), range 20-78 years). ECG data were sampled at 128 Hz.

The data for the congestive heart failure group were obtained from twenty-four hour Holter monitor recordings of forty-three subjects (including twenty-eight men and fifteen women, aged 55.5±11.4 years (mean±SD), range 22-78 years). New York Heart Association (NYHA) functional classification is provided for each subject: 4 subjects were assigned to class I, 8 to class II, 17 to class III and 14 to class III-IV. Fourteen recordings were sampled at 250 Hz, and twenty-nine recordings were sampled at 128 Hz.

The data for the atrial fibrillation group were obtained from ten hour Holter monitor recordings sampled at 250 Hz of nine subjects. Datasets were filtered to exclude artifacts, premature ventricular complexes, and missed beat detections. Of note, the inclusion of the premature ventricular complexes does not qualitatively change the MSE analysis.

Figure 5:
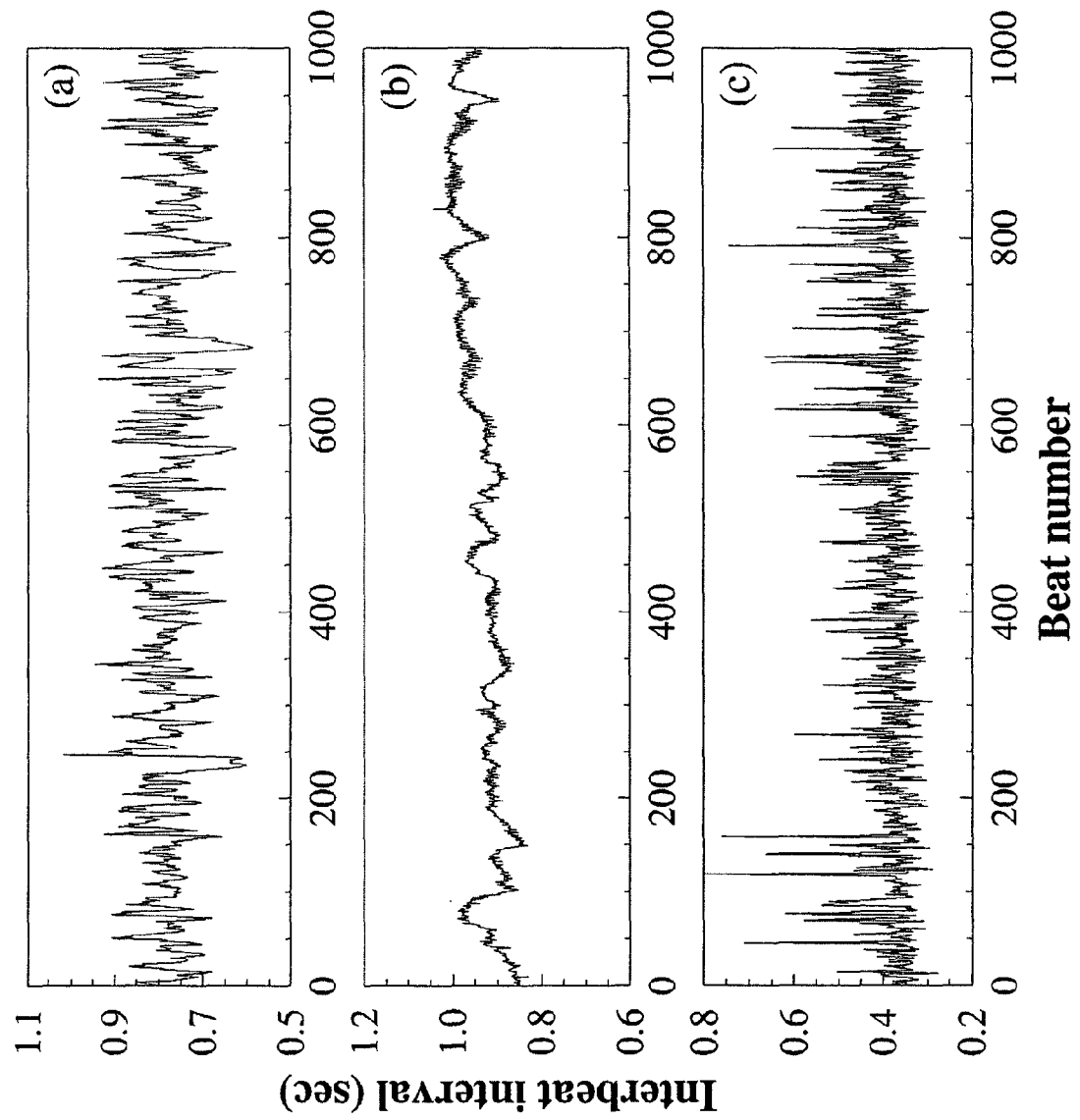
FIG. 5 illustrates a cardiac interbeat interval time series from healthy and unhealthy subjects.

FIG. 5 shows representative time series of healthy subjects (top panel), subjects with congestive heart failure (middle panel), and subjects with atrial fibrillation (lower panel). When discussing the MSE results of cardiac interbeat interval time series, reference to "large" and "small" time scales are made when the scales are larger or smaller, respectively, than one typical respiratory cycle length, that is, for example, approximately five cardiac beats.

Figure 6:
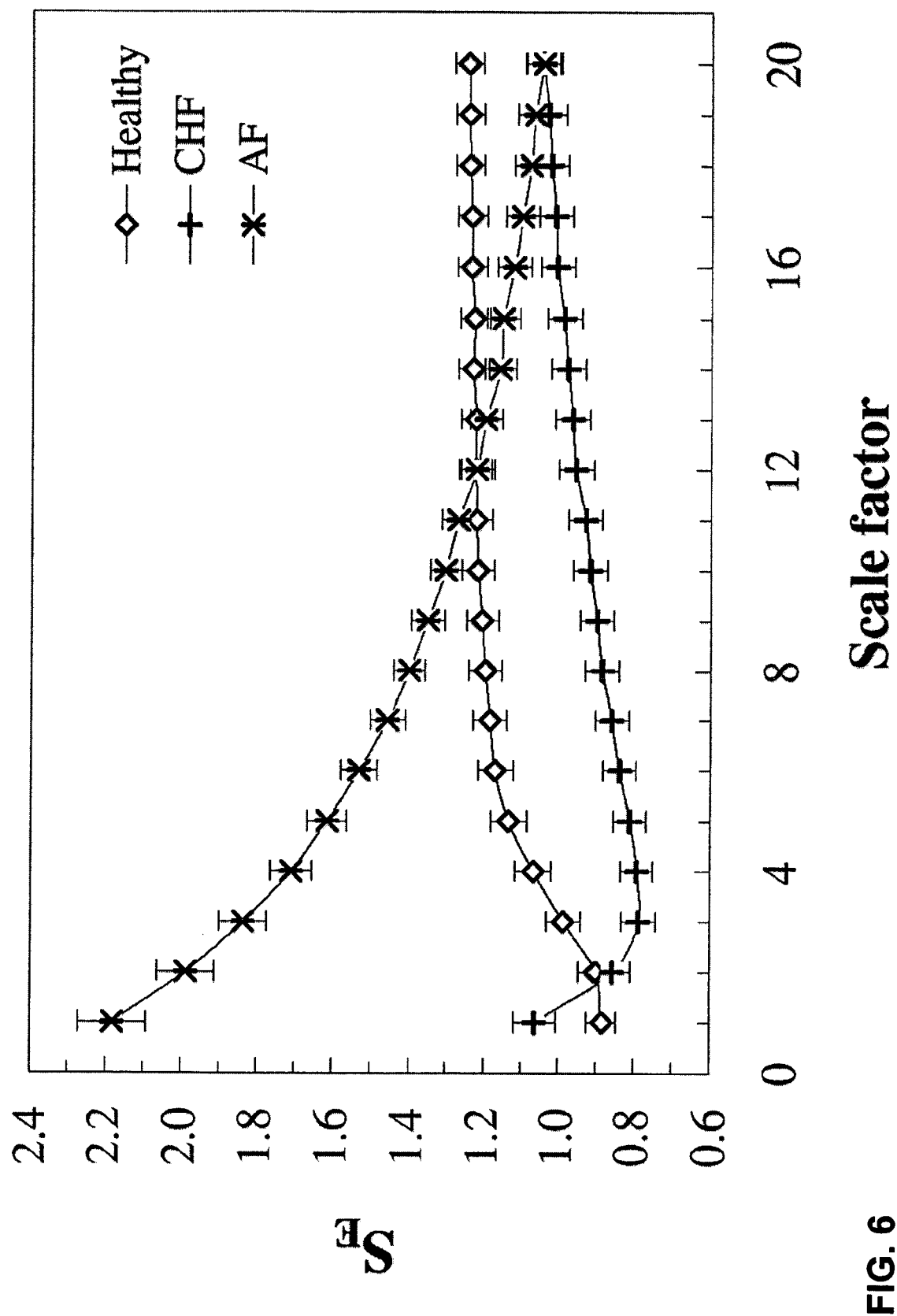
FIG. 6 illustrates an MSE analysis of interbeat interval time series obtained from 72 healthy subjects, 43 patients with heart failure and 9 subjects with atrial fibrillation. Symbols represent mean values of sample entropy and error bars represent standard errors.

In FIG. 6, the results of an MSE analysis are presented for the RR interval time series for the three groups of subjects. Three different types of behaviors can be observed. First, the entropy measure for the time series derived from healthy subjects increases on small time scales, and then stabilizes to a relatively constant value. Second, the entropy measure for the time series derived from subjects with congestive heart failure markedly decreases on small time scales, and then gradually increases. Third, the entropy measure for the time series derived from subjects with atrial fibrillation monotonically decreases, similar to white noise.

For scale one, which is the only scale considered by conventional single-scale based methods, the entropy assigned to the heartbeat time series of subjects with atrial fibrillation and those with congestive heart failure is higher than the entropy assigned to the time series of healthy subjects. In contrast, for sufficiently large scales, the time series of healthy subjects are assigned the highest entropy values. Thus, the MSE approach indicates that healthy dynamics are the most complex, contradicting the results obtained using the conventional entropy algorithms.

The time series of subjects with atrial fibrillation exhibit substantial variability in beat-to-beat fluctuations. However, the monotonic decrease of the entropy with scale reflects the degradation of the control mechanisms regulating heart rate on larger time scales in this pathologic state.

The asymptotic value of entropy may not be sufficient to differentiate time series that represent the output of different dynamical processes. Referring back to FIG. 6, for time scale 20, the values of the entropy measure for the heart failure (sinus rhythm) and atrial fibrillation time series are the same. However, these time series represent the output of very different types of cardiac dynamics. Therefore, not only the specific values of the entropy measure but also their dependence on time scale need to be taken into account to better characterize the physiologic process.

Figure 7:
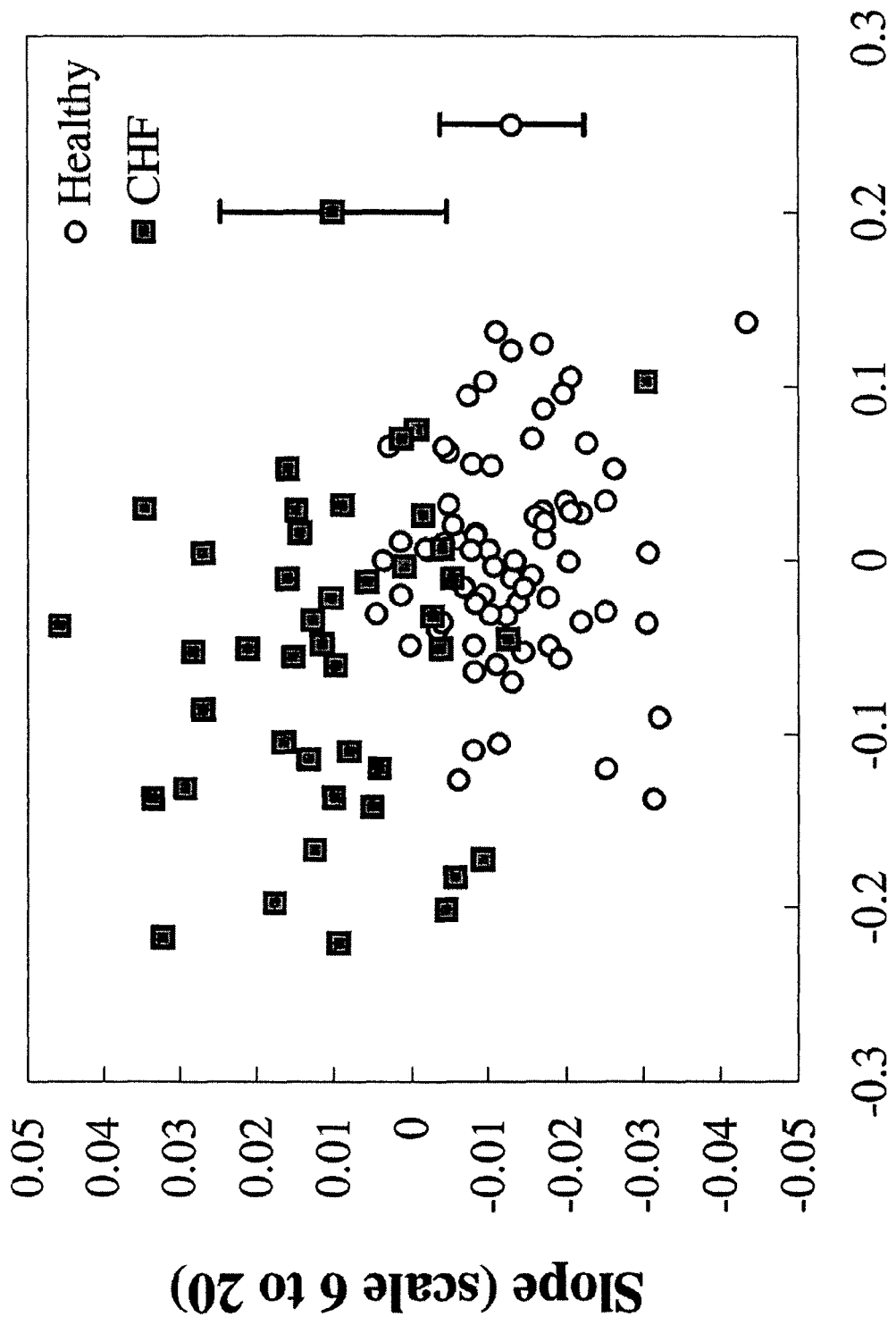
FIG. 7 illustrates the slopes of the MSE curves for small and large time scales obtained from the group of subjects analyzed in FIG. 6.

In FIG. 7, two features of the MSE curves, shown in FIG. 6, are extracted. The features are the slopes for small and large time scales (i.e., the slopes of the curves defined by the sample entropy values between scale factors 1 and 5, and scale factors 6 and 20, respectively). As can be seen, there is a notable separation between the two groups. Considering other features of the MSE curves, in addition to these slopes, may further improve the separation. Alternatively methods derived from pattern recognition techniques (e.g. Fisher's discriminant) may also be useful for clinical discrimination.

Note that the cardiac analyses reported herein pertain to interbeat interval dynamics under free-running conditions. The high capability of healthy systems to adapt to a wide range of perturbations requires functioning in a multidimensional state space. However, under stress, the system is forced to work in a tighter regime. For example, during physical exercise, there is a sustained increase in heart rate and a decrease in the amplitude of the interbeat interval fluctuations in response to an increased demand for oxygen and nutrients. The dynamics are, therefore, limited to a subset of the state space. It is anticipated that under a variety of stressed conditions, healthy systems will generate less complex outputs than under free-running conditions.

FIGS. 8-11 present the MSE results of the analysis of the RR interval time series from a randomly selected subset of the NIH Cardiac Arrhythmia Suppression Trial (CAST) RR interval sub-study database (http://physionet.org) comprising thirty subjects. Ten of the subjects received encainide, ten received flecainide, and ten received moricizine, with less than 7% premature ventricular beats. FIG. 8A shows the MSE results for the pre-treatment (PRE) and the on-therapy (POST) RR time series from a representative subject of those who received encainide. FIG. 9A shows the MSE results for the PRE and POST RR time series from a representative subject of those receiving flecainide. FIG. 10A shows the MSE results for the PRE and POST RR time series from a representative subject of those receiving moricizine.

The complexity index (CI) is defined as the area under the MSE curve. FIGS. 8B, 9B and 10B show the complexity indexes before (PRE) and after (POST) the treatment onset with the drugs encainide, flecainide and moricizine, respectively. In all cases but two in each group of treatment the complexity of the system decreased after the initiation of the therapy. Significant differences ($p<0.05$) between the complexity indexes before and after treatment onset were obtained from the one-tailed paired Wilcoxon test for the results presented in FIGS. 8, 9, and 10. The null hypothesis is that the complexity indexes for pre-treatment (PRE) and on-therapy (POST) are drawn from populations with the same mean and standard deviation.

In another embodiment, the MSE method can be used to test for an increase in physiologic complexity as a predictor of beneficial therapeutic effects for non-pharmaceutical therapy. For example, recently, Collins and colleagues (See A. Priplata, J. Niemi, J. Harry, L. Lipsitz, and J. Collins, "Vibrating insoles and balance control in elderly people," Lancet, Vol. 362, pp. 1123-1124, Oct. 4, 2003, available at www.thelancet.com, which is incorporated herein by reference) showed that the application of subsensory noise to the sole of the feet of young and elderly subjects enhances sensory and motor function, possibly via a stochastic resonance type of mechanism. The application of noise was associated with a reduction in the amount of postural sway variability in the elderly group.

Based on the concept that healthy systems are the most complex, the inventors applied the MSE method to the analysis of the 30-second sway time series derived from 15 young and 12 elderly healthy subjects under baseline conditions and with subsensory noise. These datasets are available at the open-access PhysioNet website (hht://physionet.org/physiobank/nesfdb). Young subjects did 20 trials: 10 with subsensory noise and 10 without. Elderly subjects did 10 trials: 5 with subsensory noise and 5 without. FIG. 11A presents the MSE results for the young subjects, while FIG. 11B presents the MSE results for the elderly subjects. Symbols represent mean sample entropy values for all subjects, all trials, and error bars represent standard errors.

As FIG. 11B shows, the complexity significantly ($p<0.05$) increases with the application of subsensory noise to the soles of the feet in the elderly group. These results are consistent with traditional stabilogram measures that indicate an increase of postural stability with subsensory noise. Furthermore, the MSE analysis predicts a beneficial therapeutic intervention leads to an increase of dynamical complexity Parameter Values for MSE Computations For a discussion on the optimal selection of m and r parameters, and the confidence intervals of sample entropy estimates, see D. E. Lake et al., American Journal of Physiology, 283, R789 (2002), which is incorporated herein by reference. For $m=2$ and $r=0.15$, the discrepancies between the mean values of the sample entropy for simulated time series and the numerically calculated values are less than 1% for both 1/f and white noises. This result suggests that for most practical applications the error bars associated with the computation of sample entropy values are likely smaller than the error bars related to experimental sources and also to inter- and intra-subject variability.

Effect of Noise, Outliers, and Sample Frequency in MSE Computation

For a time series sampled at frequency f, the temporal location of the actual heartbeat can be identified only up to the accuracy of $\Delta=1/f$. Each data point of a coarse-grained heartbeat interval time series is an average of consecutive differences. For example: $y_1^\tau=(RR_1+ \ldots +RR_{\tau-1})/\tau = [(t_2-t_1)+ \ldots +(t_\tau-t_{\tau-1})]=(t_\tau-t_1)/\tau$. Therefore, the accuracy of averaged heartbeat intervals of coarse-grained time series is $\Delta/\tau$, i.e., the accuracy increases with scale.

Sample entropy is underestimated for finite sample frequency values. However, the discrepancy between the value of the sample entropy calculated for a time series sampled at a finite frequency and the value of the sample entropy (SE) corresponding to the limit ($\lim_{\Delta \to 0}$ SE) decreases with scale. For analysis on small time scales it may be important to consider a correction of this effect. However, the conclusions presented herein are not altered by the value of sample frequency.

MSE Analysis of Discrete Time Series

The MSE approach can be applied to discrete time series, such as DNA sequences. Consider an uncorrelated random variable "X" with alphabet $\Theta=\{0, 1\}$. Both symbols occur with probability 1/2. All possible different 2-component sequences built from the binary series are: 00, 01, 10 and 11. Therefore, the alphabet of the coarse-grained time series corresponding to scale 2 is: $\Theta_2=\{0, 1/2, 1\}$. The probabilities associated with the occurrence of the different values are: 1/4, 1/2 and 1/4, respectively.

Assuming that the r value used to calculate the sample entropy is 0.5, only the distance between the coarse-grained values 0 and 1 (and not between values 0 and 1/2, and between 1/2 and 1) is higher than r. Therefore, the probability of distinguishing two data points randomly chosen from the coarse-grained time series, Pr ($|x_a-x_b|>r$), is "$p(0) \times p(1)=1/4 \times 1/4=1/16=0.0625$."

Similarly, there are eight different 3-component sequences that can be built from the original binary series: 000, 001, 010, 100, 110, 011, 101 and 111. Consequently, the alphabet of the coarse-grained time series corresponding to scale 3 is: $\Theta_3=\{0, 1/3, 2/3, 1\}$ and the probabilities associated with the occurrence of each value are 1/8, 3/8, 3/8, 1/8, respectively. For $r=0.5$, only the distances between the coarse-grained data points 0 and 2/3, 1/3 and 1, and 0 and 1 are higher than r. Therefore, Pr $(|x_a-x_b|>r)=p(0)\times p(2/3)+p(1/3)\times p(1)+p(0)\times p(1)=0.1094$.

FIG. 12 illustrates the probability of distinguishing any two data points randomly chosen from the coarse-grained time series of a binary discrete time series, having an r value of 0.5. Note that the probability of distinguishing two data points of the coarse-grained time series increases from scale 2 to scale 3. As a consequence, the sample entropy also increases, contrary to the results obtained from the analytic derivation of the sample entropy values for white noise time series. This artifact, which affects discrete time series, is due to the fact that the size of the alphabet of the coarse-grained time series increases with scale.

In general, for scale n, the alphabet set is: $\Theta_n=\{i/n\}$ with $0\leq i\leq n$, and the corresponding probability set, $\{p(i/n)\}$ is generated by the expression: $n!/(2^n \times i!(n-i)!)$, $0\leq i\leq n$. The value of $P_r (|x_a-x_b|>r)$ is calculated by the equation:

$$P_r(|x_a - x_b| > r) = \sum_{j=0}^{N-1} p(j/n) \sum_{i=1}^{n} p(i/n)$$

where, i=N+j+1 if n=2N (even scales), and i=N+j if n=2N−1 (odd scales).

FIG. 12 shows how the probability varies with the scale factor, and an attenuated oscillation, which as a consequence also shows up on the MSE output curve for the same time series. The period of this oscillation depends only on the r value.

To overcome this artifact, one approach is to select the scales for which the entropy values are either local minima or maxima of the MSE curve. This procedure was adopted to calculate the complexity of coding versus non-coding DNA sequences (see FIG. 14).

An alternative approach is to map the original discrete time series to a continuous time series, for example, by counting the number of symbols (1's or 0's) in nonoverlapping windows of length $2^n$. Since this procedure is not a one-to-one mapping, some information encoded on the original time series is lost. Therefore, relatively long time series are required. As discussed below with reference to FIG. 13, this procedure was adopted to calculate the complexity of binary time series derived from a computer executable file and a computer data file.

Application of MSE to Artificial and Biological Coding

In another embodiment of the present invention, the MSE approach is applied to binary sequences of artificial and biological codes, aimed at quantifying the complexity of coding and non-coding deoxyribonucleic acid (DNA) sequences. In all cells, from microbes to mammals, proteins are responsible for most structural, catalytic and regulatory functions. Therefore, the number of protein-coding genes that an organism makes use of could be an indicator of its degree of complexity. However, several observations contradict this reasoning.

Large regions of DNA, which in humans account for about 97% of the total genome, do not code for proteins and were previously thought to have no relevant purpose. These regions have been referred to "junk" DNA or gene "deserts." However, these non-coding sequences are starting to attract increasing attention as more recent studies suggest that they may have an important role in regulation of transcription, DNA replication, chromosomal structure, pairing, and condensation.

Detrended fluctuation analyses have revealed that non-coding sequences contained long-range correlations and possessed structural similarities to natural languages, suggesting that these sequences could in fact carry important biological information. In contrast, coding sequences have been found to be more like a computer data file than a natural language.

The biological implications of the presence of long-range correlations in non-coding sequences, their origin, and nature are still being debated. Audit et al. have investigated the relation between long-range correlations and the structure and dynamics of nucleosomes (see B. Audit et al., Phys. Rev. Lett. 86, 2471, (2001); and B. Audit et al., J. Mol. Biol. 316, 903 (2002), which are both incorporated herein by reference). Their results suggest that long-range correlations extending from 10 to 200 base pair (bp) are related to the mechanisms underlying the wrapping of DNA in the nucleosomal structure.

Gene regulatory elements or enhancers are types of functional sequences that reside in non-coding regions. Until recently, enhancers were thought to be located near the genes that they regulate. However, subsequent in vivo studies have demonstrated that enhancers and the genes to which they are functionally linked may be separated by more than thousands of bases. These results reinforce earlier evidence that the non-coding sequences contain biological information and further support the notion that, there are several "layers" of information in genomic DNA.

The MSE approach, as described above, can be applied to analyze the complexity of both coding and non-coding DNA sequences of human chromosomes. However, because of possible parallelisms between artificial and biological codes, first, two examples of artificial language sequences are considered. The first example is a compiled version of the LINUX Operating System (an executable computer program), and the second example is a compressed non-executable computer data file. Both can be analyzed as binary sequences.

Although both files contain useful information, the structure of that information is very different. The sequence derived from the executable program exhibits long-range correlations, while the sequence derived from the data file does not. These results indicate that the computer program, which executes a series of instructions and likely contains several loops running inside each other, possesses a hierarchical structure, in contrast to the computer data file. Therefore, the former is expected to be more complex than the latter.

When applied to discrete sequences (binary codes), the MSE results present a typical artifact due to the dependence of the entropy values on the size of the sequence alphabet. To overcome this artifact, one approach is to map the original time series to a continuous time series, for example, by counting the number of symbols (1's or 0's) in nonoverlapping windows of length $2^n$. Since this procedure is not a one-to-one mapping, some information encoded on the original time series is lost. Therefore relative long time series are required. This procedure was adopting in calculating the complexity of binary time series derived from a computer executable file and a computer data file.

The results of an MSE analysis for binary time series from a computer executable file and a computer data file are illustrated in FIG. 13. First, for scale 1, the sequence derived from the data file is assigned a higher entropy value than the sequence derived from the executable program. Second, between scales 2 and 6, the sample entropy measure does not separate the coarse-grained sequences of the two files. Additionally, for scales larger than scale 6, the highest entropy values are assigned to coarse-grained sequences derived from the executable program file. Furthermore, the difference between the sample entropy values assigned to coarse-grained sequences of the executable file and the computer data file increases with scale factor. These results indicate that the structure of the executable file is more complex than the structure of the data file. Of note, conventional (single scale) entropy algorithms applied to sequences of artificial languages fail to meaningfully quantify their overall complexity.

An alternative approach to overcome the artifact on the MSE curves of discrete time series is to select the scales for which the entropy values are either local minima or maxima of the MSE curve. This procedure was adopted in calculating the complexity of coding versus noncoding DNA sequences as illustrated in FIG. 14.

The DNA building units are four nucleotides. Two of them contain a purine base (adenine (A) or guanine (G)), and the other two contain a pyrimidine base (cytosine (C) or thymine (T)). There are many ways of mapping the DNA sequences to a numerical sequence that take into consideration different properties of the DNA sequences. For this application, the purine-pyrimidine rule was considered. Given the original DNA sequence, bases A and C are mapped to number 1, and bases C and T are mapped to number −1.

The results of an MSE analysis for coding and noncoding human DNA sequences on GenBank database, available as of June 2004 and, 30 binary random time series are illustrated in FIG. 14, according to an embodiment of the present invention. For scales larger than scale 7, sample entropy values for non-coding sequences are higher than for coding sequences. Consistently, for all scales but the first one, the lowest sample entropy values are assigned to coarse-grained time series derived from uncorrelated white noise mapped to a binary sequence. These results show that the structure of non-coding sequences is more complex than the structure of coding sequences analyzed here.

These findings suggest a parallelism between executable computer programs and non-coding sequences, and data storing files and coding sequences. They also support the view that non-coding sequences contain important biological information. Biological complexity and phenotype variations, and therefore the MSE approach of the present invention, should relate not only to proteins, which are the main effectors of cellular activity, but also to the organizational structure of the control mechanisms responsible for the networking and integration of gene activity.

Time Asymmetry Analysis of Physiologic Complexity

As discussed above, time asymmetry is another dynamical measurement that can be applied to quantify different aspects of physiologic complexity and information content. Living systems are subject to mass, energy, entropy, and information fluxes across their boundaries. These open systems function in conditions far from equilibrium. They utilize energy to evolve to more hierarchically ordered structural configurations and less entropic states in comparison with the surrounding environment. Loss of self-organizing capability can be a marker of pathology. In extreme cases presaging death, a state approaching maximum equilibrium is reached.

Time asymmetry (also referred to herein as "time irreversibility") is defined as a lack of invariance of the statistical properties under the operation of temporal inversion. Time irreversibility is a fundamental property of nonlinear, non-equilibrium systems. Surprisingly, relatively little work has been published on practical implementation of time reversibility to biologic time series.

It can be shown that: 1) time irreversibility is greatest for healthy physiologic systems, which exhibit the most complex dynamics; and 2) time irreversibility decreases with aging or pathology, providing a marker of loss of functionality and adaptability. Therefore, quantitative measurements of time irreversibility can be of basic and practical importance.

A number of computational measures of time irreversibility have been proposed and applied to physiologic and physical time series. These conventional measures, however, are all single scale-based. In contrast, complex biologic systems typically exhibit spatio-temporal structures over a wide range of scales. Therefore, the present invention provides a time irreversibility measure that incorporates information from multiple scales. The present invention can be applied to both physical and physiologic time series.

Consider the time series $X=\{x_1, x_2, \ldots, x_N\}$ and let "$\tau$" be an integer number representing the time lag between two data points. This time series is processed to compute multiple coarse-grained time series according to the equation $y_\tau(i) = (x_{\tau+i} - x_i)/\tau$ with $i \leq N-\tau$.

A measure of temporal irreversibility is defined by the equation:

$$a(\tau) = \frac{\int_0^\infty [\rho(y_\tau)\ln\rho(y_\tau) - \rho(-y_\tau)\ln\rho(-y_\tau)]^2 \, dy_\tau}{\int_{-\infty}^\infty \rho(y_\tau)\ln\rho(y_\tau) \, dy_\tau},$$

where $\rho(y_\tau)$ represents the probability distribution function of the coarse-grained time series for scale $\tau$. The time series is reversible if and only if $a(\tau)=0$.

For biologic systems, it is not only important to quantify the degree of irreversibility of a time series but also to know which time series represents the "forward" direction and which is time reversed. $a(\tau)$ does not provide that information. Thus the following quantity is defined instead:

$$A(\tau) = \frac{\int_0^\infty [\rho(y_\tau)\ln\rho(y_\tau) - \rho(-y_\tau)\ln\rho(-y_\tau)] \, dy_\tau}{\int_{-\infty}^\infty \rho(y_\tau)\ln\rho(y_\tau) \, dy_\tau}$$

If $A(\tau)>0$ then for scale $\tau$ the time series is irreversible. However, if $A(\tau)=0$, the time series may or may not be irreversible for scale $\tau$.

Real-world signals, such as heart rate time series, are sampled at a finite frequency, in which case $y_\tau$, is a discrete variable. For the analysis of these signals the following equation provides an estimator of $A(\tau)$:

$$\hat{A}(\tau) = \frac{\sum_{y_\tau>0} Pr(y_\tau)\ln[Pr(y_\tau)]}{\sum_{y_\tau} Pr(y_\tau)\ln[Pr(y_\tau)]} - \frac{\sum_{y_\tau<0} Pr(y_\tau)\ln[Pr(y_\tau)]}{\sum_{y_\tau} Pr(y_\tau)\ln[Pr(y_\tau)]},$$

where $Pr(y_\tau)$ denotes the probability of the value $y_\tau$.

In an embodiment, the multiscale asymmetry index ($A_I$) is computed from the following equation:

$$A_I = \sum_{\tau=1}^L \hat{A}(\tau).$$

Referring to FIG. 15, flowchart 1500 represents the general operational flow of an embodiment of the present invention. More specifically, flowchart 1500 shows an example of a control flow for quantifying physiologic complexity from time irreversibility measurements.

The control flow of flowchart 1500 begins at step 1501 and passes immediately to step 1503. At step 1503, a series of physiologic data is gathered from non-invasive and/or invasive measurements taken from a subject. For example, data can be taken from a twenty-four hour continuous ECG Holter monitor recording, and used to derive an RR interval time series.

At step 1506, the physiologic time series data is processed to compute multiple coarse-grained time series as described above. At step 1509, the value of $\hat{A}(\tau)$ is calculated for each coarse-grained time series. At step 1512, the multiscale asymmetry index ($A_I$) is computed as the area under the asymmetry curve $\hat{A}(\tau)$.

At step 1515, the $A_I$ metric is compared to a threshold parameter. The threshold parameter is an $A_I$ measurement produced from a physiologic time series representative of a normal or healthy subject. The computed $A_I$ (from step 1515) and the threshold $A_I$ are compared to analyze the relative degree of temporal irreversibility of the two time series.

If the $A_I$ is higher for the threshold $A_I$ than for the computed $A_I$, control passes to step 1518, and loss of temporal irreversibility is detected. Otherwise, control passes to step 1521, and no loss of temporal irreversibility is detected. If the $A_I$ is higher for the computed $A_I$ than for the threshold $A_I$, an increase in complexity is determined. Afterwards, the control flow ends as indicated at step 1595.

Referring back to step 1512, note that the $A_I$ metric corresponds to the area between the solid and dotted curves shown in FIGS. 16A-16D.

In an embodiment, the time asymmetry approach can be used to quantify the effects of drug and non-pharmacologic intervention. As such, interventions that enhance system time asymmetry (as detected at step 1521) are associated with therapeutic effects, and interventions that degrade system time asymmetry (as detected at step 1518) are associated with adverse effects.

FIG. 16 illustrates the multiscale time irreversibility (asymmetry) analysis of the cardiac interbeat interval sequences derived from twenty-four hour Holter monitor recordings of representative subjects. The scale factor is referenced to heartbeat number. FIG. 16 presents the $A_I$ values for groups of 26 healthy young subjects (FIG. 16A), 46 healthy elderly subjects (FIG. 16B), 43 patients with congestive heart failure (FIG. 16C) and 9 subjects with atrial fibrillation (FIG. 16D).

The data used for the time asymmetry analysis was obtained from an open-access database that is available at: http://www.physionet.org/physiobank/database/. As can be inferred from FIGS. 16A-16E, the time asymmetry index $A_I$ (i.e., the area between the two curves) is higher for the healthy young subjects than for both healthy elderly subjects and the subjects with pathology. Furthermore, the lowest $A_I$ values are assigned to the subjects with pathology. Note that, conventional (single scale-based) time asymmetry measures do not yield consistent differences.

Consistent results have been obtained from another study conducted with twenty-six healthy young subjects ($A_I$=0.54±0.20, mean±standard deviation), forty-six healthy elderly subjects ($A_I$=0.37±0.22), forty-three CHF subjects ($A_I$=0.09±0.29), and nine subjects with atrial fibrillation ($A_I$=0.00±0.02). Differences between groups are significant ($p<0.005$, t-test), with the exception of the two pathologic states (CHF vs. atrial fibrillation). Cardiac interbeat interval time series obtained during the sleeping period yield comparable results. Therefore, nonstationarities due to physical activity do not account for these asymmetry properties.

The results are compatible with the general concept that time irreversibility degrades with aging and disease over multiple time scales. Of note, both highly irregular heartbeat time series (such as those from subjects with atrial fibrillation) and less variable, more regular time series (such as those from heart failure subjects) tend to be more time symmetric than time series derived from healthy subjects.

The inventors have tested the hypothesis that cardiac interbeat interval time series of healthy subjects have greater time asymmetry than artificial time series generated by algorithms designed to model heart rate dynamics. To test the hypothesis, the time asymmetry approach has been applied to a database of fifty time series that is available from the PhysioNet/Computers in Cardiology Challenge 2002: RR Interval Time Series Modeling. As predicted, the asymmetry index was determined to be higher for physiologic time series than for the synthetic ones. This finding indicates that the proposed models do not fully account for the non-equilibrium properties of the control mechanisms that regulate heart rate under healthy conditions.

Multiscale time irreversibility analysis of time series provides information not extractable from conventional methods, including entropy measures and spectral techniques. This approach can be useful for both the development of realistic models of physiologic control and for bedside diagnostics, since time asymmetry is a fundamental property of healthy, far from equilibrium systems.

Information-Based Similarity Analysis of Physiologic Complexity

As discussed above, information-based similarity (IBS) is another dynamical measurement that can be applied to quantify different aspects of physiologic complexity and information content. Complex physiologic signals can carry unique dynamical signatures that are related to their underlying mechanisms. The information-based similarity approach is based on rank order statistics of symbolic sequences to investigate the profile of different types of physiologic dynamics. This approach provides a quantitative metric to define distances among the symbolic sequences.

The information-based similarity approach can be applied to heart rate fluctuations (the output of a central physiologic control system). This approach robustly discriminates patterns generated from healthy and pathologic states, as well as aging. Furthermore, an increased randomness is observed in the heartbeat time series with physiologic aging and pathologic states, and also nonrandom patterns have been uncovered in the ventricular response to atrial fibrillation.

As discussed above, physiologic systems generate complex fluctuations in their output signals that reflect the underlying dynamics. Therefore, finding and analyzing hidden dynamical structures of these signals are of both basic and clinical interest. According to embodiments of the present invention, the information-based similarity approach detects and quantifies such temporal structures in the human heart rate time series using tools from statistical linguistics.

Human cardiac dynamics are driven by the complex nonlinear interactions of two competing forces: sympathetic stimulation which increases heart rate and parasympathetic stimulation which decreases heart rate. For this type of intrinsically noisy system, it may be useful to simplify the dynamics via mapping the output to binary sequences, where the increase and decrease of the interbeat intervals are denoted by 1 and 0, respectively. The resulting binary sequence retains important features of the dynamics generated by the underlying control system, but is tractable enough to be analyzed as a symbolic sequence.

Referring to FIG. 17, flowchart 1700 represents the general operational flow of an embodiment of the present invention. More specifically, flowchart 1700 shows an example of a control flow for quantifying physiologic complexity from information-based similarity measurements.

The control flow of flowchart 1700 begins at step 1701 and passes immediately to step 1703. At step 1703, two time series of physiologic data are gathered from non-invasive and/or invasive measurements taken from the same subject or from different subjects depending on the aims of the study. If the study is aimed at characterizing changes in the system's dynamics over time or accessing the effects of an intervention, the two time series are gathered from measurements taken from the same subject at two different time points. In contrast, the time series are gathered from measurements taken from different subjects, when the study is aimed at comparing the outputs generated by different systems. The data can, for example, be taken from two readings of a twenty-four hour continuous ECG Holter monitor recording, and used to derive two RR interval time series.

At step 1706, each original time series is mapped to a binary time series. In the case of heartbeat time series each pair of successive interbeat intervals are mapped to the symbols 0 or 1, according to the equation:

$$I_n = \begin{cases} 0, & \text{if } x_n \leq x_{n-1}, \\ 1, & \text{if } x_n > x_{n-1}, \end{cases}$$

where $x_i$ is the $i^{th}$ interbeat interval. In this case, the symbols 0 and 1 represent an increase and a decrease in heart rate, respectively.

In an embodiment, "m+1" successive intervals are mapped to a binary sequence of length m, which herein is referred to as an "m-bit word." Each m-bit word "$w_k$", therefore, represents a unique pattern of fluctuations in a given time series.

At step 1709, a collection of m-bit words ($x_i$, $x_{i+1}$, ... $x_{i+m-1}$) with $1 \leq i \leq N-m+1$ are produced. It is plausible that the occurrence of these m-bit words reflects the underlying dynamics of the original time series since different types of dynamics produce different distributions of these m-bit words.

Step 1706 and step 1709 can be further explained with reference to FIG. 18, which illustrates a mapping procedure for 8-bit words from part of a two hour heartbeat time series. The symbol 0 represents a decrease between a pair of successive interbeat intervals, and the symbol 1 represents an increase between a pair of successive interbeat intervals. As shown, nine successive intervals are mapped to a binary sequence representing each 8-bit word. For example, the first word is shown as "11000110", the second word is "10001100", the third word is "00011001", and so forth. As described in greater detail below, the occurrence of these 8-bit words reflects the underlying dynamics of the original time series.

In studies of natural languages, it has been observed that different authors have a preference for the words they use with higher frequency. To apply this concept to symbolic sequences mapped from the interbeat interval time series, at step 1712, the occurrences of different words are counted, and at step 1715, the different words are sorted according to descending frequency. The resulting rank-frequency distribution, therefore, represents the statistical hierarchy of symbolic words of the original time series. For example, the first ranked word corresponds to one type of fluctuation that is the most frequent pattern in the time series. In contrast, the last ranked word defines the most unlikely pattern in the time series.

Steps 1712 and 1715 can be further explained with reference to FIGS. 19 and 20. FIG. 19 illustrates a probability distribution of every 8-bit word from the time series analyzed in FIG. 18. The word index ranges from 0 to $2^{m-1}$ for m-bit words. For the example analyzed in FIG. 19, the length m is eight, and there is a total of 256 possible words.

FIG. 20 illustrates a rank ordered probability plotted on a log-log scale. The linear regime (for rank $\leq 50$) is reminiscent of Zipf's law for natural languages. Referring back to step 1712 and step 1715, the occurrence of the different 8-bit words (from FIG. 18) are counted in FIG. 19, and the words are sorted according to descending frequency in FIG. 20.

After a rank-frequency distribution (see FIG. 20) has been produced for both time series from step 1703, control passes to step 1718. At step 1718, a measurement of similarity between the two signals is defined by plotting the rank number of each m-bit word in the first time series against that of the second time series. FIG. 21 illustrates a rank order comparison of two cardiac interbeat interval time series from the same subject. If two time series are similar in their rank order of the words, the scattered points would be located near the diagonal line. Therefore, the average deviation of these scattered points away from the diagonal line is a measure of the "distance" between these two time series. Greater distance indicates less similarity and vice versa.

In an embodiment, the likelihood of each word is incorporated in the following definition of a weighted distance "$D_m$" between two symbolic sequences, $S_1$ and $S_2$:

$$D_m(S_1 S_2) = \frac{\sum_{k=1}^{2^m} |R_1(w_k) - R_2(w_k)| p_1(w_k) p_2(w_k)}{(2^m - 1) \sum_{k=1}^{2^m} p_1(w_k) p_2(w_k)}$$

The expressions "$p_1(w_k)$" and "$R_1(w_k)$" represent probability and rank of a specific word "$w_k$" in time series $S_1$. Similarly, "$p_2(w_k)$" and "$R_2(w_k)$" stand for probability and rank of the same m-bit word in time series $S_2$. The absolute difference of ranks is multiplied by the normalized probabilities as a weighted sum and divided by the value $2^{m-1}$ to keep the $D_m$ value in the same range of [0, 1]. After the similarity measurement has been computed, the control flow ends as indicated at step 1795.

As discussed in greater detail below, it can be shown that the distance measurement ($D_m$) can be applied to identify unique dynamical patterns associated with an individual. This similarity measurement can also be applied to identify characteristic patterns that describe the dynamical structures of different physiologic or pathologic states. As a healthy system changes, with disease and aging, quantifiable changes can be detected in the dynamical patterns related to the degradation of the integrative control systems.

In an embodiment, where time series were gathered from a group of prototypically healthy subjects (group A) and from a group of patients before (group B) and after an intervention (group C), the distances between all different pairs of signals are calculated. Next, the intergroup distances are calculated.

The intergroup distance between groups A and B is defined as the average distance between all pairs of signals where one is from group A and the other from group B. A phylogenetic tree is then generated according to the distances between different groups. The further apart from the group of prototypically healthy subjects, the less complex will be a time series.

In an embodiment, the information-based similarity approach can be used to quantify the effects of drug and non-pharmacologic interventions. As such, interventions that enhance system complexity are associated with therapeutic effects, and that interventions that degrade system complexity are associated with adverse effects.

The information-based similarity measurement has been tested on subject data located in databases available at the website www.physionet.org/. (See A. L. Goldberger et al., Circulation 101, E215 (2000), which is incorporated herein by reference). The databases include forty ostensibly healthy subjects with subgroups of young (including ten females and ten males, average 25.9 years) and elderly (including ten females and ten males, average 74.5 years). The databases also include a group of forty-three subjects with severe congestive heart failure (including fifteen females and twenty-eight males, average 55.5 years), and a group of nine subjects with atrial fibrillation. All subjects in the healthy and atrial fibrillation groups have two hour recordings. The CHF group has longer data sets (i.e., 16-to-24 hours for each subject). Only an analysis for the case m=8 is presented herein. However, similar results have been obtained for the cases m=4-to-12.

First, the information-based similarity measurements was applied to the database data to examine whether the distance for subsets of the time series from the same subject is closer than that for the time series from different subjects under similar physiologic states. Each subject's time series were divided into two subsets to measure the distance between these two subsets.

The distance (e.g., $D_m$) was calculated between each pair of subjects who belong to the same group. The "intrasubject distance" represents average distances measured between two subset time series from the same subject. The "intragroup distance" represents average distances between two different subjects from the same group.

For the group of healthy young subjects, the intrasubject distance is 0.056±0.050 (mean±standard deviation), and the intragroup distance is 0.161±0.106. For the group of healthy elderly subjects, the intrasubject distance is 0.077±0.052, and the intersubject distance is 0.209±0.110. For the group of subject with congestive heart failure, the intrasubject distance is 0.053±0.047, and the intersubject distance is 0.100±0.062. Finally for the group of subjects with atrial fibrillation, the intrasubject distance is 0.046±0.015, and the intersubject distance is 0.045±0.012. These results show that the intrasubject distances are indeed smaller than the intragroup distances. The small intrasubject distances indicate that there are unique dynamical patterns associated with each individual at small time scales. The only exception is for the atrial fibrillation group. It is difficult to distinguish one subject having atrial fibrillation from another based on the rank order distance. This result is consistent with previous studies showing that, on small time scales ($\leq 200$ s), heart rate fluctuations of subjects having atrial fibrillation do not exhibit consistent structures.

Measuring the average distance between subjects across different groups, it can be seen that distances between subjects across groups are typically greater than distances between subjects within a group. This result supports the notion that there are dynamical patterns for different physiologic or pathologic states. However, there is overlap among groups. The intergroup distances are calculated among all groups from the databases as well as a group of 100 artificial time series of uncorrelated noise (white noise group).

The method for constructing phylogenetic trees is a useful tool to present the above results since the algorithm arranges different groups on a branching tree to best fit the pairwise distance measurements. FIG. 22 shows the result of a rooted tree for the case of m=8. The tree has been generated according to the distances between five groups, namely healthy young subjects, healthy elderly subjects, CHF subjects, atrial fibrillation subjects, and white noise indicating a simulated uncorrelated random time series. The distance between any two groups is the summation of the horizontal lengths along the shortest path on the tree that connects them. For example, the distance is 0.211 between healthy young and healthy elderly groups.

The structure of the tree is consistent with the underlying physiology: the farther down the branch the more complex the dynamics are. The groups are arranged in the following order (from bottom to top as shown in FIG. 22). First, the time series from the healthy young group represents dynamical fluctuations of a highly complex integrative control system. Second, the healthy elderly group represents a slight deviation from the "optimal" youthful state, possibly due to the decoupling (or dropout) of components in the integrative control system. Third, severe damage to the control system is represented by the CHF group. These individuals have profound abnormalities in cardiac function associated with pathologic alterations in both the sympathetic and the parasympathetic control mechanisms that regulate beat-to-beat variability. Fourth, the atrial fibrillation group is an example of a pathologic state in which there appears to be very limited external input on the heartbeat control system. Finally, the artificial white noise group represents the extreme case in that only noise and no signal is present.

A further application of the rank order distance concept is to quantify the degree of nonrandomness. To this end, a surrogate time series is generated by random shuffling of the original time series. Random shuffling of the data yields exactly the same distribution of the original interbeat intervals sequence, but destroys their sequential ordering. The distance (i.e., $D_m$) between an interbeat interval time series and its randomized surrogate provides an index of the nonrandomness of the time series.

FIG. 23 illustrates a heartbeat interval time series from a healthy subject showing complex variability. In contrast, a time series from a CHF subject (as illustrated in FIG. 24) shows less variability. FIG. 25 shows a rank order comparison of the time series in FIG. 23. As can be seen for healthy subjects, the rank map between each original signal and its randomized surrogate shows prominent scatter. The measured nonrandomness is 0.31.

FIG. 26 shows a rank order comparison of the time series in FIG. 24. In contrast to FIG. 25, heart rate dynamics with CHF show rank maps with relatively narrow distributions indicating that fluctuations in CHF are closer to random (nonrandomness index=0.10).

Next, the information-based similarity measurement is applied to calculate nonrandomness distances that correspond to different word lengths "m" ranging from two to twelve. FIG. 27 shows the result for m=8. For healthy and CHF subjects, there are significant differences ($p<10^{-4}$) in this nonrandomness index over the entire range of "m" studied. However, the nonrandomness distance of the healthy young group is only significantly higher than that of the healthy elderly group at the scale m=3 ($p<0.05$), suggesting a preservation of most of the nonrandom features of heart rate dynamics with physiologic aging. Subjects with atrial fibrillation also show significantly higher values of the nonrandomness index than white noise over the range of $5 \leq m \leq 9$ ($p<10^{-4}$). Therefore, even on small time scales, the information-based similarity measurements can effectively discriminate certain data sets of the atrial fibrillation group from white noise, whereas conventional methods have not been successful in this regard.

Another attractive feature of rank order statistics is that the method is useful in examining the details of the underlying dynamics. For example, the nonrandomness test indicates a significant difference between atrial fibrillation and uncorrelated noise. The rank numbers of the "words" that contribute to this difference from white noise can be further analyzed. The assumption is that if a word dramatically changes its rank after randomization (shuffling), the fluctuations mapped by this word may not be random and could contain relevant structural information. After systemically reviewing all atrial fibrillation recordings, the words that are significantly different from random sequences, occurring in a subset of these subjects, are given as (00100100), (00110001), (00101000), and (01000100). This finding suggests hidden structural organization in the short-term variation of the ventricular rhythm in atrial fibrillation. These sequences need further systematic analysis, in conjunction with information from intracardiac electrophysiologic studies, to elucidate the mechanism of the ventricular response to atrial fibrillation in different settings.

Thus, the information-based similarity approach introduces a quantitative metric to define distances among symbolic sequences. In application to the heart rate time series, this approach provides new quantitative information that is not measured by conventional heart rate variability techniques. This method can be easily adapted to other physiologic and physical time series provided that a meaningful mapping to symbolic sequences can be obtained. Finally, this linguistic-type method is potentially useful because of its ability to take into account both macroscopic structures and the microscopic details of the dynamics.

In another embodiment, the invention is used to assess the stability of the output of non-biologic networks. For example, the invention can be used to assess the stability of the output of the global Internet, a wide area network (WAN), a local area network (LAN), a Web server, other telecommunications networks, electricity flow in a power grid, as well as systems for managing air traffic flow, automotive traffic flow, shipping traffic in busy sea ports, rail traffic flow, and the like. In such environments, a loss of complexity in the output of the system may be a marker of a breakdown of network stability and possibly of an impending catastrophic failure. Thus, while the invention is described above primarily in biologic environments, the invention has wide application in non-biologic environments.

For example, in the environment of the global Internet, the fluctuations of network traffic under normal ("healthy") conditions should exhibit higher levels of complexity as measured by MSE compared with those under pathologic conditions related to virus attack or other intrinsic or extrinsic disruptions.

Exemplary Computer System Implementation

FIGS. 1-27 provide an exemplary environment for describing various exemplary embodiments of the present invention. It should be understood that embodiments of the present invention could be implemented in hardware, firmware, software, or a combination thereof. In such an embodiment, portions of the various components and steps would be implemented in hardware, firmware, and/or software to perform the functions of the present invention. That is, the same piece of hardware, firmware, or module of software could perform one or more of the illustrated blocks (i.e., components or steps).

The present invention can be implemented in one or more computer systems capable of carrying out the functionality described herein. Referring to FIG. 28, an example computer system 2800 useful in implementing the present invention is shown. Various embodiments of the invention are described in terms of this example computer system 2800. After reading this description, it will become apparent to one skilled in the relevant art(s) how to implement the invention using other computer systems and/or computer architectures.

The computer system 2800 includes one or more processors, such as processor 2804. The processor 2804 is connected to a communications infrastructure 2806 (e.g., a communications bus, crossover bar, or network).

Computer system 2800 can include a display interface 2802 that forwards graphics, text, and other data from the communications infrastructure 2806 (or from a frame buffer not shown) for display on the display unit 2830.

Computer system 2800 also includes a main memory 2808, preferably random access memory (RAM), and can also include a secondary memory 2810. The secondary memory 2810 can include, for example, a hard disk drive 2812 and/or a removable storage drive 2814, representing a floppy disk drive, a magnetic tape drive, an optical disk drive, etc. The removable storage drive 2814 reads from and/or writes to a removable storage unit 2818 in a well-known manner. Removable storage unit 2818, represents a floppy disk, magnetic tape, optical disk, etc., which is read by and written to removable storage drive 2814. As will be appreciated, the removable storage unit 2818 includes a computer usable storage medium having stored therein computer software (e.g., programs or other instructions) and/or data.

In alternative embodiments, secondary memory 2810 can include other similar means for allowing computer software and/or data to be loaded into computer system 2800. Such means can include, for example, a removable storage unit 2822 and an interface 2820. Examples of such can include a program cartridge and cartridge interface (such as that found in video game devices), a removable memory chip (such as an EPROM, or PROM) and associated socket, and other removable storage units 2822 and interfaces 2820, which allow software and data to be transferred from the removable storage unit 2822 to computer system 2800.

Computer system 2800 can also include a communications interface 2824. Communications interface 2824 allows software and data to be transferred between computer system 2800 and external devices. Examples of communications interface 2824 can include a modem, a network interface (such as an Ethernet card), a communications port, a PCMCIA slot and card, etc. Software and data transferred via communications interface 2824 are in the form of signals 2828 which can be electronic, electromagnetic, optical, or other signals capable of being received by communications interface 2824. These signals 2828 are provided to communications interface 2824 via a communications path (i.e., channel) 2826. Communications path 2826 carries signals 2828 and can be implemented using wire or cable, fiber optics, a phone line, a cellular phone link, an RF link, free-space optics, and/or other communications channels.

In this document, the terms "computer program medium" and "computer usable medium" are used to generally refer to media such as removable storage unit 2818, removable storage unit 2822, a hard disk installed in hard disk drive 2812, and signals 2828. These computer program products are means for providing software to computer system 2800. The invention is directed to such computer program products.

Computer programs (also called computer control logic or computer readable program code) are stored in main memory 2808 and/or secondary memory 2810. Computer programs can also be received via communications interface 2824. Such computer programs, when executed, enable the computer system 2800 to implement the present invention as discussed herein. In particular, the computer programs, when executed, enable the processor 2804 to implement the processes of the present invention, such as the various steps of methods 100, 200, 1600, and 2200, for example, described above. Accordingly, such computer programs represent controllers of the computer system 2800.

In an embodiment where the invention is implemented using software, the software can be stored in a computer program product and loaded into computer system 2800 using removable storage drive 2814, hard drive 2812, interface 2820, or communications interface 2824. The control logic (software), when executed by the processor 2804, causes the processor 2804 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to one skilled in the relevant art(s).

In yet another embodiment, the invention is implemented using a combination of both hardware and software.

The foregoing description of the specific embodiments will so fully reveal the general nature of the invention that others can, by applying knowledge within the skill of the art (including the contents of the documents cited and incorporated by reference herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the art.

It should also be understood the each of the documents and Internet websites referenced above are incorporated herein by reference as if reproduced in full below.

While various embodiments of the present invention have been described above, it should be understood that they have been presented by way of example, and not limitation. It will be apparent to one skilled in the relevant art(s) that various changes in form and detail can be made therein without departing from the spirit and scope of the invention. Thus, the present invention should not be limited by any of the above-described exemplary embodiments, but should be defined only in accordance with the following claims and their equivalents.

What is claimed is:

1. A method of assessing stability of a network based on a series of data associated with the network, comprising:
   analyzing the series of data to produce a measure of complexity, wherein the analyzing includes:
      computing a multiple coarse-grained time series from the series of data,
      calculating a sample entropy measure from the multiple coarse-grain time series, and
      plotting the sample entropy measure as a function of a scale factor to thereby produce a multiscale sample entropy curve;
   comparing the complexity measure to a control, wherein the comparing includes:
      comparing the multiscale sample entropy curve to a threshold curve to thereby detect loss, gain, or consistency in complexity; and
   assessing the stability of the network based on the comparison of the complexity measure to the control,
   wherein the analyzing, comparing and assessing are performed by one or more processors.

2. The method of claim 1, wherein the comparing step further comprises:
   comparing the multiscale sample entropy curve to a threshold curve, wherein the threshold curve is taken at a prior time.

3. The method of claim 1, wherein the comparing step further comprises:
   comparing the multiscale sample entropy curve to a threshold curve, wherein the threshold curve is taken from a different network.

4. The method of claim 1, wherein the analyzing step further comprises:
   analyzing the series of data, wherein the series of data is from a network selected from the group consisting of a global Internet, a wide area network, a local area network, a Web server, a telecommunications network, a power grid, air traffic flow, automotive traffic flow, shipping traffic flow, and rail traffic flow.

5. The method of claim 1, wherein the assessing step further comprises:
   indicating a positive effect of a change to the network when a gain in complexity is detected.

6. The method of claim 1, wherein the assessing step further comprises:
   indicating a negative effect of a change to the network when a loss in complexity is detected.

7. A computer program product comprising a non-transitory computer useable medium having computer readable program code functions embedded in the medium for causing a computer to assess stability of a network based on a series of data associated with the network, comprising:
   a first computer readable program code function that causes the computer to analyze the series of data to produce a measure of complexity, including causing the computer to:
      process the series of data to produce multiple coarse-grained time series;
      calculate a degree of irreversibility of each coarse-grained time series; and
      sum the degrees of irreversibility for the coarse-grained time series to compute a multiscale time asymmetry index;
   a second computer readable program code function that causes the computer to compare the complexity measure to a control; and
   a third computer readable program code function that causes the computer to assess the stability of the network based on the comparison of the complexity measure to the control.

8. The computer program product of claim 7, wherein the second computer readable program code function comprises:
   computer readable program code function to compare the complexity measure to a control, wherein the control is selected from the group consisting of a complexity measure taken at a prior time, a complexity measure taken from a different network, and a predetermined threshold value.

9. The computer program product of claim 7, wherein the third computer readable program code function indicates a positive effect of a change to the network when a gain in complexity is detected and indicates a negative effect of the change when a loss in complexity is detected.

10. The computer program product of claim 7, wherein the second computer readable program code function compares the complexity measure to a control, wherein the multiscale time asymmetry index is the complexity measure and the control is a threshold index.

11. A computer-based system to assess stability of a network based on a series of data associated with the network, comprising:
  first means for analyzing the series of data to produce a measure of complexity, wherein the first means for analyzing includes:
    means for classifying each pair of successive intervals from the series into one of two states representing a decrease or an increase between intervals;
    means for mapping the two states to binary symbols to produce a plurality of binary words, wherein each word has a length m and is shifted one data point with respect to an adjacent word, wherein each m-bit word represents a unique pattern of fluctuation in the series; and
    means for producing a rank-frequency distribution from the plurality of m-bit words;
  second means for comparing the complexity measure to a control; and
  third means for assessing the stability of the network based on the comparison of the complexity measure to the control.

12. The computer-based system of claim 11, wherein the second means further comprises:
  means to compare the complexity measure to a control, wherein the control is selected from the group consisting of a complexity measure taken at a prior time, a complexity measure taken from a different network, and a predetermined threshold value.

13. The computer-based system of claim 11, wherein the third means indicates a positive effect of a change to the network when a gain in complexity is detected and indicates a negative effect of the change when a loss in complexity is detected.

14. The computer-based system of claim 11, wherein the second means compares the rank-frequency distribution to a threshold rank-frequency distribution for a second series of data to thereby detect loss, gain, or consistency in complexity.

* * * * *